United States Patent
Weber et al.

(10) Patent No.: US 11,938,010 B2
(45) Date of Patent: *Mar. 26, 2024

(54) ABSORBENT CORE, ARTICLES COMPRISING SAID CORE, AND METHODS OF MAKING

(71) Applicants: ONTEX BV, Buggenhout (BE); ONTEX GROUP NV, Erembodegem (BE)

(72) Inventors: Ainas Weber, Bad Neuenahr-Ahrweiler (DE); Manfred Breu, Luxem (DE); Christel Mailinger, Elz (DE); Thomas Heege, Düngenheim (DE)

(73) Assignees: ONTEX BV, Buggenhout (BE); ONTEX GROUP NV, Erembodegem (BE)

(*) Notice: Subject to any disclaimer, the term of this patent is extended or adjusted under 35 U.S.C. 154(b) by 373 days.

This patent is subject to a terminal disclaimer.

(21) Appl. No.: 16/917,308

(22) Filed: Jun. 30, 2020

(65) Prior Publication Data

US 2020/0330293 A1 Oct. 22, 2020

Related U.S. Application Data

(63) Continuation of application No. 16/473,862, filed as application No. PCT/EP2017/084195 on Dec. 21, 2017, now Pat. No. 10,729,599.

(30) Foreign Application Priority Data

Dec. 27, 2016 (EP) ..................................... 16206993
Sep. 27, 2017 (BE) ................................... 2017/0132

(51) Int. Cl.
*A61F 13/532* (2006.01)
*A61F 13/15* (2006.01)
(Continued)

(52) U.S. Cl.
CPC ...... *A61F 13/532* (2013.01); *A61F 13/15658* (2013.01); *A61F 13/42* (2013.01);
(Continued)

(58) Field of Classification Search
CPC ...... A61F 13/53; A61F 13/533; A61F 13/534; A61F 13/532; A61F 13/4756; A61F 13/539
See application file for complete search history.

(56) References Cited

U.S. PATENT DOCUMENTS 4,079,739 A * 3/1978 Whitehead ........ A61F 13/15674
604/389
5,433,715 A   7/1995 Tanzer et al.
(Continued)

FOREIGN PATENT DOCUMENTS

DE   102013019314 A1   5/2015
EP        0597273 A1   5/1994
(Continued)

OTHER PUBLICATIONS

Communication Pursuant to Article 94(3) EPC in European Application No. 16206993.4, dated Nov. 29, 2018.
(Continued)

*Primary Examiner* — Jessica Arble
(74) *Attorney, Agent, or Firm* — VIVICAR Law, PLLC

(57) ABSTRACT

An absorbent core comprising substantially continuous zones of one or more high fluid distribution structures and discontinuous zones of fluid absorption structures surrounding the one or more high fluid distribution structures, wherein the one or more high fluid distribution structures are arranged to distribute fluid across the absorbent core at a speed that is faster than the speed of fluid distribution across the absorbent core by said discontinuous fluid absorption structures, and wherein said continuous zones extend along
(Continued)

a path that is substantially parallel to at least a portion of the perimeter of the core, said portion of the perimeter of the core comprising at least a portion of the sides of the core and one of the ends of the core.

22 Claims, 16 Drawing Sheets

(51) Int. Cl.
| | |
|---|---|
| A61F 13/42 | (2006.01) |
| A61F 13/475 | (2006.01) |
| A61F 13/531 | (2006.01) |
| A61F 13/533 | (2006.01) |
| A61F 13/534 | (2006.01) |
| A61F 13/539 | (2006.01) |
| B32B 37/02 | (2006.01) |
| B32B 37/10 | (2006.01) |
| B32B 37/14 | (2006.01) |
| B32B 37/22 | (2006.01) |
| A61F 13/53 | (2006.01) |
| B29D 99/00 | (2010.01) |
| B29K 23/00 | (2006.01) |

(52) U.S. Cl.
CPC ........ *A61F 13/4756* (2013.01); *A61F 13/531* (2013.01); *A61F 13/533* (2013.01); *A61F 13/534* (2013.01); *A61F 13/539* (2013.01); *B32B 37/02* (2013.01); *B32B 37/1018* (2013.01); *B32B 37/142* (2013.01); *B32B 37/22* (2013.01); *A61F 13/1565* (2013.01); *A61F 2013/15926* (2013.01); *A61F 2013/423* (2013.01); *A61F 2013/530131* (2013.01); *A61F 2013/530481* (2013.01); *A61F 2013/530868* (2013.01); *A61F 2013/53908* (2013.01); *B29D 99/0064* (2013.01); *B29K 2023/00* (2013.01); *B29K 2713/00* (2013.01)

(56) References Cited

U.S. PATENT DOCUMENTS

| | | | |
|---|---|---|---|
| 5,756,039 A | 5/1998 | McFall et al. | |
| 6,503,233 B1 | 1/2003 | Chen et al. | |
| 7,666,174 B2 | 2/2010 | Onishi et al. | |
| 7,718,021 B2 | 5/2010 | Venturino et al. | |
| 9,216,116 B2 | 12/2015 | Roe et al. | |
| 10,729,599 B2* | 8/2020 | Weber .................. | A61F 13/531 |
| 2002/0052587 A1* | 5/2002 | Magnusson .......... | A61F 13/535 |
| | | | 604/385.101 |
| 2004/0122398 A1 | 6/2004 | Schnabel et al. | |
| 2006/0116652 A1 | 6/2006 | Miura et al. | |
| 2006/0184150 A1 | 8/2006 | Noel | |
| 2007/0073253 A1* | 3/2007 | Miyama .............. | A61F 13/4704 |
| | | | 604/385.101 |
| 2007/0246147 A1 | 10/2007 | Venturino et al. | |
| 2009/0281511 A1 | 11/2009 | Fukae | |
| 2010/0051166 A1 | 3/2010 | Hundorf et al. | |
| 2010/0121303 A1 | 5/2010 | Kudo et al. | |
| 2011/0319855 A1 | 12/2011 | Lash | |
| 2012/0312491 A1 | 12/2012 | Jackels et al. | |
| 2012/0316046 A1 | 12/2012 | Jackels et al. | |
| 2013/0060218 A1 | 3/2013 | Kudo et al. | |
| 2013/0123729 A1* | 5/2013 | Minami .............. | A61F 13/5611 |
| | | | 604/380 |
| 2013/0131622 A1 | 5/2013 | Sukegawa | |
| 2013/0165884 A1* | 6/2013 | Kawakami .......... | A61F 13/4756 |
| | | | 604/379 |
| 2013/0176312 A1 | 7/2013 | Schouwenburg et al. | |
| 2013/0218115 A1 | 8/2013 | Katsuragawa et al. | |
| 2014/0039437 A1 | 2/2014 | Van de Maele | |
| 2015/0065975 A1* | 3/2015 | Roe ................... | A61F 13/49001 |
| | | | 604/374 |
| 2015/0080837 A1 | 3/2015 | Rosati et al. | |
| 2015/0088084 A1 | 3/2015 | Baker et al. | |
| 2015/0223991 A1 | 8/2015 | Jackels | |
| 2015/0313766 A1 | 11/2015 | Miao et al. | |
| 2015/0342796 A1 | 12/2015 | Bianchi et al. | |
| 2016/0206482 A1 | 7/2016 | Nishikawa et al. | |
| 2016/0346136 A1 | 12/2016 | Strasemeier et al. | |
| 2019/0000693 A1 | 1/2019 | Shima et al. | |
| 2019/0183688 A1 | 6/2019 | Suzuki | |
| 2019/0262193 A1 | 8/2019 | Konawa | |
| 2019/0343691 A1 | 11/2019 | Weber et al. | |

FOREIGN PATENT DOCUMENTS

| | | |
|---|---|---|
| EP | 0781537 A1 | 7/1997 |
| EP | 1077052 A1 | 2/2001 |
| EP | 1078617 A2 | 2/2001 |
| EP | 1088536 A2 | 4/2001 |
| EP | 1267775 B1 | 9/2004 |
| EP | 1349524 B1 | 1/2010 |
| EP | 2277482 A1 | 1/2011 |
| EP | 2211808 B1 | 10/2012 |
| EP | 2532329 A1 | 12/2012 |
| EP | 1959903 B1 | 2/2014 |
| EP | 2886093 A1 | 6/2015 |
| EP | 2905000 A1 | 8/2015 |
| EP | 3238679 A1 | 11/2017 |
| JP | 2012096079 A | 5/2012 |
| WO | 2015031229 A1 | 3/2015 |
| WO | 2016104277 A1 | 6/2016 |
| WO | 2016114947 A1 | 7/2016 |

OTHER PUBLICATIONS

International Search Report and Written Opinion for PCT/EP2017/084195; dated Mar. 26, 2018.
International Search Report and Written Opinion for PCT/EP2017/084604; dated Mar. 7, 2018.

* cited by examiner

ABSORBENT CORE, ARTICLES COMPRISING SAID CORE, AND METHODS OF MAKING

CROSS-REFERENCE TO RELATED APPLICATIONS

This application is a continuation of U.S. application Ser. No. 16/473,862, filed Jun. 26, 2019, which is the national stage application of corresponding international application number PCT/EP2017/084195, filed Dec. 21, 2017, which claims priority to and the benefit of European application no. 16206993.4, filed Dec. 27, 2016, and Belgian application no. 2017/0132, filed Sep. 27, 2017, all of which are hereby incorporated by reference in their entirety.

TECHNICAL FIELD

The disclosure pertains to the technical field of absorbent hygiene products. In particular, the present disclosure relates to an absorbent core that can be used within an article for absorbing body fluids and exudates, such as urine and fecal material, or blood, menses, and vaginal fluids. More particularly, the present disclosure relates to absorbent garments, such as disposable diapers or diaper pants, disposable incontinence diapers or pants, and which are configured to collect and contain fecal material and avoid leakage, or sanitary napkins or panty liners, which are configured to collect and contain blood, menses, urine, vaginal fluids and avoid leakage.

BACKGROUND

The disclosure relates to an absorbent core for an absorbent article, in particular for hygiene articles, to absorbent articles comprising said absorbent core and to processes for providing said absorbent core. In particular to cores having one or more channels therethrough.

Absorbent cores have been subject to considerable improvement and innovation over time to address needs such as improved fluid absorption and distribution, as well as comfort, and a need for continued improvement exists. Such needs are ever present in today's demanding consumer environment. The following paragraphs elucidate on some of the relevant disclosures pertaining to this subject.

EP 1077052 A1 and EP 1078617 A2 disclose a sanitary napkin allowing controlled deformation in response to lateral compression when in use. The sanitary napkin has preferential bending zones extending along a longitudinal axis formed by a process of perforating, slitting, cutting or embossing.

EP 1959903 B1 discloses an incontinence pad comprising a pair of folding lines dividing the absorbent core material into a central portion and a pair of longitudinal side portions to adapt better to the body of the user. The folding lines are formed by compression of the absorbent material.

EP 2211808 B1 discloses an absorbent core comprising an upper absorbent core and a lower absorbent core. The upper absorbent core comprises fold indications enabling the absorbent core to adopt a predetermined three-dimensional shape when subjected to pressure in the width direction. The fold indications are cuts or compression lines which do or do not extend completely through the upper core.

EP 1349524 B1 discloses a pantiliner comprising at least one fold line defining a central area and two side areas which allows adjusting the size of the pantiliner by folding the pantiliner along the fold line. The fold lines are lines of embossing.

EP 1267775 B1 discloses a sanitary pad that conforms to the body confinements. The sanitary pad comprises a forward wide portion and a rear narrow portion and at least two fold lines preformed on the upper or lower surface of the narrow portion. The fold lines may be selected from mechanically pressed lines, chemically joined constituents forming the lines, heat generated lines, laser generated lines, adhesive generated lines and/or mechanical vibration generated lines.

EP1088536 A2 discloses a hygiene napkin provided with corrugations making it possible to adapt the hygienic napkin to the user's panties.

U.S. Pat. No. 5,756,039 A discloses an absorbent core comprising distinct segments which can be independently displaced by a lifting member. The lifting member ensures that the top sheet conforms to the wearer's body.

US 2006/0184150 A1 discloses an absorbent core with varying flexibility that act as shaping element for improved body fit. The absorbent core can have lines of reduced bending resistance which are formed by removal of material, e.g. in the form of apertures or slots.

U.S. Pat. No. 6,503,233 B1 discloses an absorbent article comprising a combination of downwardly-deflecting crease lines and an upward-deflecting shaping line to achieve a geometry for improved body fit. The crease lines are formed by embossing of the absorbent material. The shaping line is formed by perforation or notching.

US 2015/0088084 A1, discloses a method of making an absorbent structure having a three-dimensional topography including placing at least a portion of the absorbent structure between opposed mold surfaces. At least one of the mold surfaces has a three-dimensional topography. The three-dimensional topography of the mold surface is imparted onto the absorbent structure so that the absorbent structure has a three-dimensional topography corresponding to the three-dimensional topography of the mold surface.

However, there remains a need in the art for improved cores and methods of making that not only can increase the fluid absorption characteristics of the product but also provides for longer lasting dryness and comfort, as well as providing a perception to the user of said improved characteristics.

The present disclosure aims to resolve at least some of the problems mentioned above.

The present disclosure aims to provide a novel absorbent core having channels particularly designed to improve uniform liquid distribution and comfort; an absorbent article comprising the same; and an effective process of making such cores in a simplified, reliable, reproducible, and cost-effective manner.

SUMMARY

In one aspect, the disclosure relates to an absorbent core comprising substantially continuous zones of one or more high fluid distribution structures and discontinuous zones of fluid absorption structures surrounding the one or more high fluid distribution structures, wherein the one or more high fluid distribution structures are arranged to distribute fluid across the absorbent core at a speed that is faster than the speed of fluid distribution across the absorbent core by said discontinuous fluid absorption structures, and wherein said continuous zones extend along a path that is substantially parallel to at least a portion of the perimeter of the core, said portion of the perimeter of the core comprising at least a portion of the sides of the core and one of the ends of the core.

In a further aspect, the disclosure relates to an absorbent core comprising: a front portion; a back portion; a crotch portion position between the front portion and the back portion; and a longitudinal axis extending along a length of said core and crossing said front, crotch and back portions, the absorbent core having a width extending perpendicular to said length and a perimeter comprising at least two opposing ends and at least two opposing sides positioned between said ends wherein the absorbent core comprises one or more substantially interconnected channels extending through at least a portion of the crotch portion along the length of the core and along at least a portion of said width of the core from one side of the core to the other, preferably said one or more substantially interconnected channels being symmetric or asymmetric about the longitudinal axis.

In a preferred aspect, the absorbent core has at least one of the interconnected channels, preferably each said channel, forming a shape having a closed end in the form of a U-bend, and preferably an open end in the form of two diverging ends or a funnel-shape, preferably wherein the closed end is positioned proximal to the back portion of the absorbent core and the open end is positioned proximal to the front portion of the absorbent core and distal from said closed end.

In a further aspect, the disclosure relates to an absorbent article comprising said core, preferably said article being selected from disposable diapers or diaper pants; disposable incontinence diapers or diaper pants; sanitary napkins; or panty liners; and typically wherein the channels in said core remain visible both before and after use of the article, preferably wherein the channels are more visible after use than before use of the article.

In yet a further aspect, the disclosure relates to the use of an absorbent core according to the disclosure in an absorbent article, for improved liquid distribution compared to the same absorbent article comprising a core free of substantially interconnected channels.

In yet a further aspect, the disclosure relates to the use of an absorbent core according to the disclosure in an absorbent article, for providing a tri-stage fluid distribution comprising a first fluid distribution at a first speed, a second fluid distribution at a second speed and a third fluid distribution at a third speed, said first speed being greater or equal to said second speed and said third speed being less than said first speed and less than or equal to said second speed, preferably wherein the first fluid distribution is driven by the substantially interconnected channels, the second fluid distribution is driven by a three-dimensional absorbent material comprised within the core, and the third fluid distribution is driven by an amount of super absorbent polymer dispersed within the three-dimensional absorbent material.

In yet a further aspect, the disclosure relates to a process of making an absorbent core comprising the steps of: providing a mold comprising a 3D insert therein, said 3D insert being the inverse shape of the desired channels, wherein substantially the entire surface of the mold is in fluid communication with an under-pressure source except for the 3D insert; applying a first nonwoven web to said mold; applying a three-dimensional absorbent material over at least a portion of said nonwoven; applying a second nonwoven web directly or indirectly over the three-dimensional absorbent material; optionally applying a bonding step to form a laminate comprising said first nonwoven, said second nonwoven and said three-dimensional absorbent material therebetween; optionally removing said laminate from the mold to form an absorbent core comprising channels having the inverse shape of said 3D insert; and wherein at least for the duration of the step of applying a three-dimensional absorbent material, the underpressure source is arranged to provide a vacuum force forcing said three-dimensional absorbent material around the 3D insert such to substantially evacuate the surface thereof from three-dimensional absorbent material and form channels substantially free of three-dimensional absorbent material.

DETAILED DESCRIPTION

Figure 1:
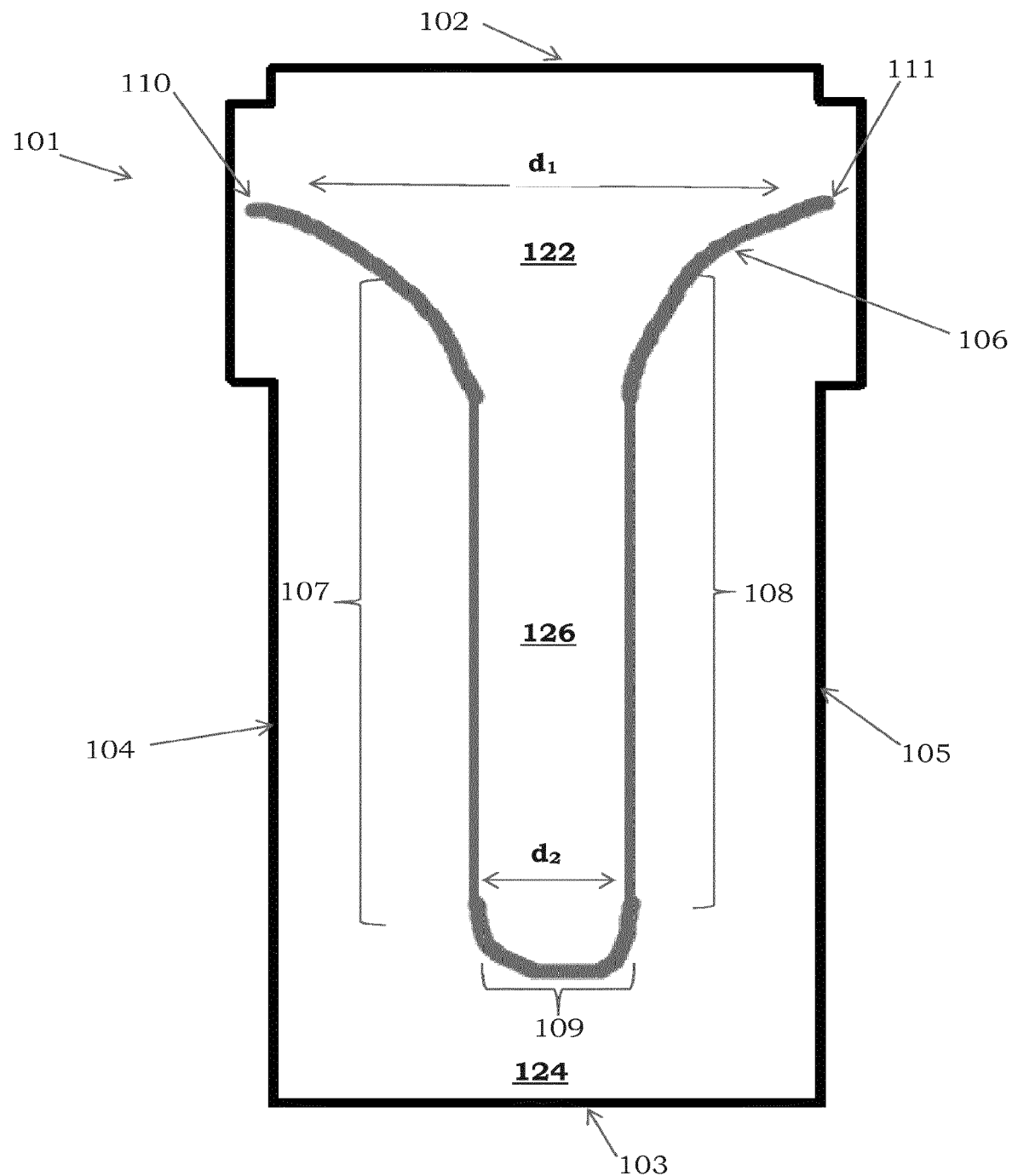
FIG. 1 shows a diagrammatic top view of an absorbent core according to an embodiment herein.

Unless otherwise defined, all terms used in disclosing characteristics of the disclosure, including technical and scientific terms, have the meaning as commonly understood by one of ordinary skill in the art to which this disclosure belongs. By means of further guidance, term definitions are included to better appreciate the teaching of the present disclosure.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed disclosure. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The expression "% by weight" (weight percent), here and throughout the description unless otherwise defined, refers to the relative weight of the respective component based on the overall weight of the formulation.

The recitation of numerical ranges by endpoints includes all numbers and fractions subsumed within that range, as well as the recited endpoints.

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinence briefs, training pants, diaper holders and liners, sanitary napkins and the like, as well as surgical bandages and sponges. Absorbent articles preferably comprise a longitudinal axis and a transversal axis perpendicular to said longitudinal axis. The longitudinal axis is hereby conventionally chosen in the front-to-back direction of the article when referring to the article being worn, and the transversal axis is conventionally chosen in the left-to-right direction of the article when referring to the article being worn. Disposable absorbent articles can include a liquid pervious top sheet, a back sheet joined to the top sheet, and an absorbent core positioned and held between the top sheet and the back sheet. The top sheet is operatively permeable to the liquids that are intended to be held or stored by the absorbent article, and the back sheet may or may not be substantially impervious or otherwise operatively impermeable to the intended liquids. The absorbent article may also include other components, such as liquid wicking layers, liquid intake layers, liquid distribution layers, transfer layers, barrier layers, wrapping layers and the like, as well as combinations thereof. Disposable absorbent articles and the components thereof can operate to provide a body-facing surface and a garment-facing surface.

An absorbent article, such as a diaper, comprises a front waistband region, a back waistband region, an intermediate crotch region which interconnects the front and rear waistband regions. When used herein, reference to a "front" portion refers to that part of the absorbent article which is generally located on the front of a subject, such as an infant or adult, when in use. Reference to the "rear" portion refers to the portion of the absorbent article generally located at the rear of the subject, such as an infant or adult, when in use, and reference to the "crotch" portion refers to that portion which is generally located between the legs of subject, such as an infant or adult, when in use. The crotch region is an area where repeated fluid surge typically occurs, within the absorbent article assembly.

"Front", "rear or back", and "crotch" portions of the absorbent core as used herein typically refer to portions of the absorbent core that are proximal to respective portions of the absorbent article. For example, the "front" portion of the core is that which is most proximal to the front of the subject when worn, the "rear or back" portion of the core is that which is most proximal to the rear or back of the subject when worn, and the "crotch" portion of the core is the middle portion of the absorbent core between the "front" and "rear or back" portions.

Preferably, a diaper comprises a liquid permeable "top sheet", a liquid impermeable "back sheet", and an "absorbent medium" disposed between the top sheet and the back sheet. The top sheet, back sheet and the absorbent medium could be made from any suitable material known to the person skilled in the art. The top sheet is generally located at or near the bodyside surface of the article, while the back sheet is generally located at or near the garment-side surface of the article. Optionally, the article may comprise one or more separate layers which are in addition to the back sheet and are interposed between the back sheet and the absorbent medium. Top sheet and back sheet are connected or otherwise associated together in an operable manner.

The "absorbent medium" or "absorbent core" or "absorbent body" is the absorbent structure disposed between the top sheet and the back sheet of the absorbent article in at least the crotch region of the absorbent article and is capable of absorbing and retaining liquid body exudates. The size and the absorbent capacity of the absorbent medium should be compatible with the size of the intended wearer and the liquid loading imparted by the intended use of the absorbent article. Further, the size and the absorbent capacity of the absorbent medium can be varied to accommodate wearers ranging from infants through adults. It may be manufactured in a wide variety of shapes (for example, rectangular, trapezoidal, T-shape, I-shape, hourglass shape, etc.) and from a wide variety of materials. Examples of commonly occurring absorbent materials are cellulosic fluff pulp, tissue layers, highly absorbent polymers (so called superabsorbent polymer particles (SAP)), absorbent foam materials, absorbent nonwoven materials or the like. It is common to combine cellulosic fluff pulp with superabsorbent polymers in an absorbent material.

"Acquisition and distribution layer", "ADL" or "surge management portion" refers to a sub-layer which preferably is a nonwoven wicking layer under the top sheet of an absorbent product, which speeds up the transport and improves distribution of fluids throughout the absorbent core. The surge management portion is typically less hydrophilic than the retention portion, and has the ability to quickly collect and temporarily hold liquid surges, and to transport the liquid from its initial entrance point to other parts of the absorbent structure, particularly the retention portion. This configuration can help prevent the liquid from pooling and collecting on the portion of the absorbent garment positioned against the wearer's skin, thereby reducing the feeling of wetness by the wearer. Preferably, the surge management portion is positioned between the top sheet and the retention portion.

The term "adhesive" as used herein is intended to refer to any suitable hot melt, water or solvent borne adhesive that can be applied to a surface of a film layer in the required pattern or network of adhesive areas to form the film-nonwoven laminate of the present disclosure. Accordingly, suitable adhesives include conventional hot melt adhesives, pressure-sensitive adhesives and reactive adhesives (i.e., polyurethane).

As used herein, the term "adhesive bonding" means a bonding process which forms a bond by application of an adhesive. Such application of adhesive may be by various processes such as slot coating, spray coating and other topical applications. Further, such adhesive may be applied within a product component and then exposed to pressure such that contact of a second product component with the adhesive containing product component forms an adhesive bond between the two components.

As used herein, an "airformed web" refers to a material comprising cellulosic fibers such as those from fluff pulp that have been separated, such as by a hammermilling process, and then deposited on a porous surface without a substantial quantity of binder fibers present. Airfelt materials used as the absorbent core in many diapers, for example, are a typical example of an airformed material.

As used herein, an "airlaid web" is a fibrous structure formed primarily by a process involving deposition of air-entrained fibers onto a mat, typically with binder fibers present, and typically followed by densification and thermal bonding. In addition to traditional thermally bonded airlaid structures (those formed with non-tacky binder material present and substantial thermally bonded), the scope of the term "airlaid" according to the present disclosure can also include coform, which is produced by combining air-entrained dry, dispersed cellulosic fibers with meltblown synthetic polymer fibers while the polymer fibers are still tacky. Further, an airformed web to which binder material is subsequently added can be considered within the scope of the term "airlaid" according to the present disclosure. Binder can be added to an airformed web in liquid form (e. g., an aqueous solution or a melt) by spray nozzles, direction injection or impregnation, vacuum drawing, foam impregnation, and so forth. Solid binder particles can also be added by mechanical or pneumatic means.

As used therein, the term "associated" encompasses configurations in which top sheet is directly joined to back sheet by affixing top sheet directly to back sheet, and configurations wherein top sheet is joined to back sheet by affixing top sheet to intermediate members which in turn are affixed to back sheet. Top sheet and back sheet can be affixed directly to each other by attachment means such as an adhesive, sonic bonds, thermal bonds or any other attachment means known in the art. For example, a uniform continuous layer of adhesive, a patterned layer of adhesive, a sprayed pattern of adhesive or an array of separate lines, swirls or spots of construction adhesive may be used to affix top sheet to back sheet. It should be readily appreciated that the above-described attachment means may also be employed to interconnect and assemble together the various other component parts of the article described herein.

The terms "back section" and "rear back section" are used herein as synonyms and refer to the area of the absorbent article which is contact with the back of the wearer when the absorbent article is worn.

The term "back sheet" refers to a material forming the outer cover of the absorbent article. The back sheet prevents the exudates contained in the absorbent structure from wetting articles such as bedsheets and overgarments which contact the disposable absorbent article. The back sheet may be a unitary layer of material or may be a composite layer composed of multiple components assembled side-by-side or laminated. The back sheet may be the same or different in different parts of the absorbent article. At least in the area of the absorbent medium the back sheet comprises a liquid impervious material in the form of a thin plastic film, e.g. a polyethylene or polypropylene film, a nonwoven material coated with a liquid impervious material, a hydrophobic nonwoven material, which resists liquid penetration, or a laminate of a plastic film and a nonwoven material. The back sheet material may be breathable so as to allow vapour to escape from the absorbent material, while still preventing liquids from passing there through. Examples of breathable back sheet materials are porous polymeric films, nonwoven laminates of spunbond and meltblown layers and laminates of porous polymeric films and nonwoven materials.

The terms "belly section" and "front belly section" are used herein as synonyms and refer to the area of the absorbent article which is contact with the belly of the wearer when the absorbent article is worn.

The term "blend" means a mixture of two or more polymers while the term "alloy" means a sub-class of blends wherein the components are immiscible but have been compatibilized.

As used herein, the "body-facing" or "bodyside" surface means that surface of the article or component which is intended to be disposed toward or placed adjacent to the body of the wearer during ordinary use, while the "outward", "outward-facing" or "garment-side" surface is on the opposite side, and is intended to be disposed to face away from the wearer's body during ordinary use. Such outward surface may be arranged to face toward or placed adjacent to the wearer's undergarments when the absorbent article is worn.

"Bonded" refers to the joining, adhering, connecting, attaching, or the like, of at least two elements. Two elements will be considered to be bonded together when they are bonded directly to one another or indirectly to one another, such as when each is directly bonded to intermediate elements.

The term "breathable" refers to films having a water vapor transmission rate (WVTR) of at least 300 grams/m$^2$-24 hours.

"Carded web" refers to webs that are made from staple fibers that are sent through a combing or carding unit, which opens and aligns the staple fibers in the machine direction to form a generally machine direction-oriented fibrous nonwoven web. The web is then bonded by one or more of several known bonding methods. Bonding of nonwoven webs may be achieved by a number of methods; powder bonding, wherein a powdered adhesive or a binder is distributed through the web and then activated, usually by heating the web and adhesive with hot air; pattern bonding, wherein heated calendar rolls or ultrasonic bonding equipment are used to bond the fibers together, usually in a localized bond pattern, though the web can be bonded across its entire surface if so desired; through-air bonding, wherein air which is sufficiently hot to soften at least one component of the web is directed through the web; chemical bonding using, for example, latex adhesives that are deposited onto the web by, for example, spraying; and consolidation by mechanical methods such as needling and hydroentanglement.

As used herein, the term "cellulosic" is meant to include any material having cellulose as a major constituent, and specifically comprising at least 50 percent by weight cellulose or a cellulose derivative. Thus, the term includes cotton, typical wood pulps, nonwoody cellulosic fibers, cellulose acetate, cellulose triacetate, rayon, thermomechanical wood pulp, chemical wood pulp, debonded chemical wood pulp, milkweed, or bacterial cellulose.

"Chassis" refers to a foundational constituent of an absorbent article upon which the remainder of the structure of the article is built up or overlaid, e.g., in a diaper, the structural elements that give the diaper the form of briefs or pants when configured for wearing, such as a back sheet, a top sheet, or a combination of a top sheet and a back sheet.

"Coform" as used herein is intended to describe a blend of meltblown fibers and cellulose fibers that is formed by air forming a meltblown polymer material while simultaneously blowing air-suspended cellulose fibers into the stream of meltblown fibers. The coform material may also include other materials, such as superabsorbent particles. The meltblown fibers containing wood fibers are collected on a forming surface, such as provided by a foraminous belt. The forming surface may include a gas-pervious material, such as spunbonded fabric material, that has been placed onto the forming surface.

"Compression" refers to the process or result of pressing by applying force on an object, thereby increasing the density of the object.

The term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, solvents, particulates and materials added to enhance processability of the composition.

The diaper can comprise "containment flaps" or "barrier cuffs". The containment flaps are generally thought to be particularly well suited for the containment of fecal matter and to prevent the lateral flow of liquid waste until such time as the liquid waste can be absorbed by the absorbent article. Many constructions of containment flaps are known. Such containment flaps generally comprise a proximal edge, intended to be attached to the absorbent article, and an opposite distal edge which is generally not attached to the absorbent article along at least a portion of its length. An elastic member is generally located adjacent the distal edge to assist in maintaining the containment flap in an upright condition and in maintaining a sealing relationship between the distal edge of the containment flap and the body of a wearer during use. The elastic member is generally located between two layers of material so that the elastic does not come into contact with the body of a wearer. The containment flaps may be manufactured from a wide variety of materials such as polypropylene, polyester, rayon, nylon, foams, plastic films, formed films, and elastic foams. A number of manufacturing techniques may be used to manufacture the containment flaps. For example, the containment flaps may be woven, non-woven, spunbonded, carded, cast, blown or the like.

The diaper can comprise leg containment gaskets. Leg "containment gaskets" help prevent leakage of bodily exudates when the wearer exerts compressive forces on the absorbent article. In particular, the stiffness of the leg containment gaskets prevents twisting and bunching of the leg openings of the absorbent article which can lead to leaks. In addition, the elasticity and conformability of the leg containment gaskets ensures that the bodyfacing surface of the leg containment gaskets provides an adequate seal against the body of the wearer. The physical properties of the leg containment gaskets, such as the thickness and stiffness, also function to space the bodyside liner, outer cover and absorbent core away from the wearer's body when in use. As such, void volume is created between the wearer's body and the bodyside liner and absorbent core of the absorbent article to help contain body exudates.

A "continuous waistband" can be an elastomeric, cloth-like, nonwoven fibrous material, such as an elastomeric stretch bonded laminate web or an elastomeric meltblown web. By proper selection of materials, the continuous waistband can be rendered temporarily elastically inhibited, such as by compression. Once temporarily elastically inhibited, the elastic material, of which waistband is comprised, can be activated, such as by treating with heat, to recover to a state of elasticity.

"Conventional hot-melt adhesive" means a formulation that generally comprises several components. These components typically include one or more polymers to provide cohesive strength (e.g., aliphatic polyolefins such as poly (ethylene-co-propylene) copolymer; ethylene vinyl acetate copolymers; styrene-butadiene or styrene-isoprene block copolymers; etc.); a resin or analogous material (sometimes called a tackifier) to provide adhesive strength (e.g., hydrocarbons distilled from petroleum distillates; rosins and/or rosin esters; terpenes derived, for example, from wood or citrus, etc.); perhaps waxes, plasticizers or other materials to modify viscosity (i.e., flowability) (examples of such materials include, but are not limited to, mineral oil, polybutene, paraffin oils, ester oils, and the like); and/or other additives including, but not limited to, antioxidants or other stabilizers. A typical hot-melt adhesive formulation might contain from about 15 to about weight percent cohesive strength polymer or polymers; from about 50 to about 65 weight percent resin or other tackifier or tackifiers; from more than zero to about 30 weight percent plasticizer or other viscosity modifier; and optionally less than about 1 weight percent stabilizer or other additive. It should be understood that other adhesive formulations comprising different weight percentages of these components are possible.

The term "density" or "concentration" when referring to the absorbent material, in particular the SAP, of a layer, refers to the amount of the absorbent material divided by the surface area of the layer over which the absorbent material is spread out.

As used herein, the term "diaper" refers to an absorbent article generally worn by infants about the lower torso.

The term "disposable" is used herein to describe absorbent articles that generally are not intended to be laundered or otherwise restored or reused as an absorbent article (i.e., they are intended to be discarded after a single use and, preferably, to be recycled, composted or otherwise disposed of in an environmentally compatible manner).

As used herein, the term "elastic resistance" describes an elastic force that tends to resist an applied tensile force causing a material provided therewith to tend to contract to an untensioned configuration in response to a stretching force.

As used herein, the terms "elastic", "elastomeric", "elasticity" or derivations thereof are used to describe the ability of various materials and objects comprised of such to reversibly undergo deformation under stress, e.g., become stretched or extended, in at least one direction when a force is applied to the material and to resume substantially to their original dimensions upon relaxing, i.e., when the force is released, without rupture or breakage. Preferably, it refers to a material or composite which can be elongated in at least one direction by at least 50% of its relaxed length, i.e., elongated to at least 150% of its relaxed length, and which will recover upon release of the applied tension at least 40% of its elongation. Accordingly, upon release of the applied tension at 50% elongation, the material or composite contracts to a relaxed length of not more than 130% of its original length. Examples of suitable elastomer materials include polyether-polyamide block copolymers, polyurethanes, synthetic linear A-B-A and A-B block copolymers, chlorinated rubber/EVA (ethylene-vinyl acetate) blends, EPDM (ethylene-propylene diene monomer) rubbers, EPM (ethylene-propylene monomer) rubbers, blends of EPDM/EPM/EVA, and the like.

The term "elasticized" refers to a material, layer, or substrate that is naturally non-elastic, but which has been rendered elastic by, for example, suitably joining an elastic material, layer, or substrate thereto.

"Elongation" means the ratio of the extension of a material to the length of the material prior to the extension (expressed in percent), as represented by the following: "Extension" means the change in length of a material due to stretching (expressed in units of length).

As used herein the term "extensible" means elongatable in at least one direction, but not necessarily recoverable.

The term "fabrics" is used to refer to all of the woven, knitted and nonwoven fibrous webs.

"Fastening means", such as tape tab fasteners, are typically applied to the back waistband region of the diaper to provide a mechanism for holding the diaper on the wearer. Fastening means, such as tape tab fasteners, snaps, pins, belts, hooks, buckles, "hook/mushroom"-and-loop fasteners (e.g. VELCRO®-type fasteners) and the like, may be employed and are typically applied at the lateral, side ends of the back waistband region of diaper to provide a mechanism for holding the diaper about the waist of the wearer in a conventional manner. Tape tab fasteners can be any of those well known in the art, and are typically applied to the corners of the diaper. For example, adhesive fasteners, mechanical fasteners, hook-and-loop fasteners, snaps, pins or buckles, may be used alone, or in combination. For example, the fasteners can be adhesive fasteners, which are constructed to releasably adhere to a landing zone patch attached to the front waistband section of the diaper to provide a refastenable adhesive fastening system.

The term "finished" or "final", when used with reference to a product, means that the product has been suitably manufactured for its intended purpose.

The term "flexible" refers to materials which are compliant and which will readily conform to the general shape and contours of the wearer's body.

As used herein, the term "garment" means any type of apparel which may be worn. This includes diapers, training pants, incontinence products, surgical gowns, industrial workwear and coveralls, undergarments, pants, shirts, jackets and the like.

Many of the known superabsorbent polymer particles exhibit gel blocking. "Gel blocking" occurs when superabsorbent polymer particles are wetted and the particles swell so as to inhibit fluid transmission to other regions of the absorbent structure. Wetting of these other regions of the absorbent member therefore takes place via a very slow diffusion process. In practical terms, this means acquisition of fluids by the absorbent structure is much slower than the rate at which fluids are discharged, especially in gush situations. Leakage from the absorbent article can take place well before the particles of SAP in the absorbent member are even close to being fully saturated or before the fluid can diffuse or wick past the "blocking" particles into the rest of the absorbent member. Gel blocking can be a particularly acute problem if the superabsorbent polymer particles do not have adequate gel strength and deform or spread under stress once the particles swell with absorbed fluid.

The term "graphic" includes, but is not limited to, any type of design, image, mark, figure, codes, words, patterns, or the like. For a product such as a training pant, graphics will generally include objects associated with little boys and little girls, such as multi-color trucks, airplanes, balls, dolls, bows, or the like.

"Hydroentanglement process" refers to the manufacturing of nonwoven webs. The process involves directing a series of water jets towards a fibrous web which is supported on a moving porous belt. The water jets pass downwards through the mass of fibres and on making contact with the surface of the belt, the jets rebound, and break up: the energy released causes entanglement of the mass of fibres.

The term "high-absorbency material" refers to materials that are capable of absorbing at least 10 times their own weight in liquid. The high-absorbency material may comprise absorbent gelling materials, such as superabsorbent polymers. Superabsorbent polymers are water-swellable, water-insoluble organic or inorganic materials capable of absorbing at least about 20 times their own weight of an aqueous solution containing 0.9 weight percent of sodium chloride. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces. Examples of synthetic absorbent gelling material polymers include the alkali metal and ammonium salts of poly(acrylic acid) and poly (methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent structure include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be used. Synthetic absorbent gelling materials typically are xerogels which form hydrogels when wetted. The term "hydrogel", however, has commonly been used to also refer to both the wetted and unwetted forms of the material. The high-absorbency material may be in any of a wide variety of geometric forms. As a general rule, it is preferred that the high-absorbency material be in the form of discrete particles. However, the high-absorbency material may also be in the form of fibres, flakes, rods, spheres, needles, spiral or semi-spiral, cubic, rod-like, polyhedral, or the like. Conglomerates of particles of high-absorbency material may also be used. The high-absorbency material may be present in the absorbent core in an amount of from about 5 to about 100 weight percent and desirably from about 30 to about 100 weight percent based on the total weight of the absorbent core. The distribution of the high-absorbency material within the different portions of the absorbent core can vary depending upon the intended end use of the absorbent core. The high-absorbency material may be arranged in a generally discrete layer within the matrix of hydrophilic fibres. Alternatively, the absorbent core may comprise a laminate of fibrous webs and high-absorbency material or other suitable means of maintaining a high-absorbency material in a localized area.

A "hook-and-loop fastener" refers to complementary fastening means having a "hook" portion and a "loop" portion and which are refastenable. The term "hook" as used herein refers to any element capable of engaging another element, the so called "loop" portion. The term "hook" is not limited to only "hooks" in its normal sense, but rather encompasses any form of engaging elements, whether unidirectional or bi-directional. The term "loop" is likewise not limited to "loops" in its normal sense, but also encompasses any structure capable of engaging with a "hook" fastener. Examples of "loop" materials are fibrous structures, like nonwoven materials.

The term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. The term "wettable" is meant to refer to a fiber which exhibits a liquid, such as water, synthetic urine, or a 0.9 weight percent aqueous saline solution, in air contact angle of less than 90°, whereas "hydrophobic" or "non-wettable" describes fibers having contact angles equal to or greater than 90°.

As used herein, the term "impermeable" generally refers to articles and/or elements that are substantially not penetrated by aqueous fluid through the entire thickness thereof under a pressure of 1.0 kPa or less. Preferably, the impermeable article or element is not penetrated by aqueous fluid under pressures of 3.4 kPa or less. More preferably, the impermeable article or element is not penetrated by fluid under pressures of 6.8 kPa or less. An article or element that is not impermeable is permeable.

"Integral" is used to refer to various portions of a single unitary element rather than separate structures bonded to or placed with or placed near one another.

"Join", "joining", "joined", or variations thereof, when used in describing the relationship between two or more elements, means that the elements can be connected together in any suitable manner, such as by heat sealing, ultrasonic bonding, thermal bonding, by adhesives, stitching, or the like. Further, the elements can be joined directly together, or may have one or more elements interposed between them, all of which are connected together.

The term "laid-flat state" is intended to refer to the article when it is flattened into a plane or is substantially flattened into a plane and is used in contrast to when the article otherwise positioned, such as when the article is folded or shaped in or for use by a wearer.

"Laminate" refers to elements being attached together in a layered arrangement.

The use of the term "layer" can refer, but is not limited, to any type of substrate, such as a woven web, nonwoven web, films, laminates, composites, elastomeric materials, or the like. A layer can be liquid and air permeable, permeable to air but impermeable to liquids, impermeable both to air and liquid, or the like. When used in the singular, it can have the dual meaning of a single element or a plurality of elements.

The crotch portion of the absorbent article preferably comprises opposite longitudinal side portions which comprise a pair of elasticized, longitudinally-extending "leg cuffs". The leg cuffs are generally adapted to fit about the legs of a wearer when in use and serve as a mechanical barrier to the lateral flow of body exudates. Leg cuffs are elasticized by leg elastics. The diaper further can comprise a front waist elastic and a rear waist elastic. Materials suitable for use in forming leg elastics are known to those skilled in the art.

Exemplary of such materials are strands or ribbons of a polymeric, elastomeric material which are adhered to the diaper at the leg cuff while in a stretched position, or which are attached to the diaper while the diaper is pleated, such that elastic constrictive forces are imparted to the leg cuff. Examples of suitable elastomer materials that can be used include polyether-polyamide block copolymers, polyurethanes, synthetic linear A-B-A and A-B block copolymers, chlorinated rubber/EVA (ethylene-vinyl acetate) blends, EPDM (ethylene-propylene diene monomer) rubbers, EPM (ethylene-propylene monomer) rubbers, blends of EPDM/EPM/EVA, and the like.

"Liquid" means a nongaseous substance and/or material that flows and can assume the interior shape of a container into which it is poured or placed.

"Longitudinal" is a direction running parallel to the maximum linear dimension of the article.

The term "meltblown fibers" means fibers formed by extruding a molten thermoplastic material through a plurality of fine, usually circular, die capillaries as molten threads or filaments into a high velocity gas stream (e.g. air) which attenuates the filaments of molten thermoplastic material to reduce their diameter, which may be to microfiber diameter. In general, meltblown fibers have an average fiber diameter of up to about 10 microns. After the fibers are formed, the meltblown fibers are carried by the high velocity gas stream and are deposited on a collecting surface to form a web of randomly disbursed meltblown fibers.

The term "nonelastic" refers to any material which does not fall within the definition of "elastic" above The term "nonwoven fabric or web" means a sheet material having a structure of individual fibers or threads which are interlaid, but not in a regular manner such as occurs with knitting or weaving processes. Nonwoven fabrics or webs have been formed from many processes such as for example, meltblowing processes, spunbonding processes, and bonded carded web processes.

"Pant body" refers to a garment that has a waist opening and a pair of leg openings, similar to shorts, swim wear, or the like. The described garment may or may not have a manually tearable side seam.

By the terms "particle", "particles", "particulate", "particulates" and the like, it is meant that the material is generally in the form of discrete units. The units can comprise granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for inclusion herein. The terms "particle" or "particulate" may also include an agglomeration comprising more than one individual particle, particulate or the like. Additionally, a particle, particulate or any desired agglomeration thereof may be composed of more than one type of material.

The term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and random symmetries.

By the term "pre-packed" as used herein, is meant that one or more absorbent articles are packed in a single unit before being stacked.

"Pulp fluff" or "fluff pulp" refers to a material made up of cellulose fibers. The fibers can be either natural or synthetic, or a combination thereof. The material is typically lightweight and has absorbent properties.

"Refastenable" refers to the property of two elements being capable of releasable attachment, separation, and subsequent releasable reattachment without substantial permanent deformation or rupture.

The "retention portion" or "liquid absorption layer" is part of the absorbent medium. This portion may comprise a matrix of hydrophilic fibers, such as a web of cellulosic fluff, mixed with particles of high-absorbency material. In particular arrangements, the retention portion may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be non-uniformly mixed. For example, the concentrations of superabsorbent particles may be arranged in a non-step-wise gradient through a substantial portion of the thickness of the absorbent structure, with lower concentrations toward the bodyside of the absorbent structure and relatively higher concentrations toward the outerside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

As used herein the term "sheet" or "sheet material" refers to woven materials, nonwoven webs, polymeric films, polymeric scrim-like materials, and polymeric foam sheeting.

The absorbent article may also contain side panels. The "side panels" can have any shape such as but not limited to square, rectangular, triangular, circular and trapezoidal shape. They can be joined to the respective opposite side portions of the back section, by a known method, such as heat-sealing or adhesive bonding. The side panels may also be formed integrally with the back section by projecting and joining together the respective top sheet and/or back sheet and/or absorbent medium outward in lugs having the shape of the side panels. Preferably, the side panels are formed by laminating a layer of nonwoven fabric, a layer of thermoplastic film and a layer of elastic material. The layer of elastic material might be sandwiched between the nonwoven fabric layer and the thermoplastic film by adhesive layers. The layer of nonwoven fabric might be made of natural fibers, synthetic fibers or a blend of natural fibers and synthetic fibers. The layer of thermoplastic film might be made of polyethylene or polypropylene.

The term "spunbond fibers" refers to fibers formed by extruding molten thermoplastic polymers as filaments or fibers from a plurality of relatively fine, usually circular, capillaries of a spinneret, and then rapidly drawing the extruded filaments by an eductive or other well-known drawing mechanism to impart molecular orientation and physical strength to the filaments. The average diameter of spunbond fibers is typically in the range of from 15-60 μm or higher. The spinneret can either be a large spinneret having several thousand holes per meter of width or be banks of smaller spinnerets, for example, containing as few as 40 holes.

The term "spunbond meltblown spunbond" (SMS) nonwoven fabric as used herein refers to a multi-layer composite sheet comprising a web of meltblown fibers sandwiched between and bonded to two spunbond layers. A SMS nonwoven fabric can be formed in-line by sequentially depositing a first layer of spunbond fibers, a layer of meltblown fibers, and a second layer of spunbond fibers on a moving porous collecting surface. The assembled layers can be bonded by passing them through a nip formed between two rolls that can be heated or unheated and smooth or patterned. Alternately, the individual spunbond and meltblown layers can be pre-formed and optionally bonded and collected individually such as by winding the fabrics on wind-up rolls. The individual layers can be assembled by layering at a later time and bonded together to form a SMS nonwoven fabric. Additional spunbond and/or meltblown layers can be incorporated in the SMS fabric, for example spunbond-meltblown-meltblown-spunbond (SMMS), etc.

"Staple fibers" refer to commercially available fibers having diameters ranging from less than about 0.001 mm to more than about 0.2 mm; they come in several different forms such as short fibers ranging from about 10 to 50 mm in length and long fibers with a length higher than 50 mm, preferably up to 100 mm.

By "stretch", it is meant that the material has the ability to extend beyond its original size in at least one dimension when subjected to a tensile force (i. e., tension) applied in the direction of that dimension, without breaking the material. An extension of for example 50% means that the material with an initial length of 100 mm has reached a length of 150 mm. Stretch may be unidirectional, bi-directional, or multi-directional. The specific stretch properties of a material may vary along any of the stretch vectors. The term can include elastic materials, as well as nonwovens that can be inherently extensible, but not necessarily in an elastic manner. Such nonwovens can be made to behave in an elastic manner by bonding them to elastic films.

By "channels", it is meant that the structure referred to (e.g. the absorbent core) comprises recessed regions forming visible conduits or passages typically extending along the longitudinal axis of the core and having a depth in a direction perpendicular to said longitudinal axis. By "visible" it is herein intended clearly visible by naked eye and typically that the channels have a width generally greater than 1 mm, preferably from 5 mm to 50 mm, more preferably from 8 mm to 40 mm, more preferably from 10 mm to 30 mm, even more preferably from greater than 10 mm to less than 25 mm.

By "interconnected", it is meant that the structure referred to (e.g. the channels) from a substantially continuous path such as from a first end of a channel to a second end of the same channel.

By "substantially", it is meant at least the majority of the structure referred to. For example, with reference to interconnected channels, "substantially interconnected" means that the majority of the channel is interconnected and generally wherein a direct and continuous path can be traced by starting from one end of the channel towards another end of the channel, said ends (also referred to herein as terminal positions) being distal to each other in a width direction of the core and proximal to a portion of the perimeter of the core, preferably the sides thereof.

By "directly over", it is meant that the feature referred to is placed over the structure referred to such that the two are in direct contact with each other at least throughout a substantial portion of said structure.

By "indirectly over", it is meant that the feature referred to is placed over the structure referred to but in such a way that the two are not in direct contact with each other at least throughout a substantial portion of said structure. For example, a nonwoven web applied indirectly over a three-dimensional absorbent material comprises a further layer of material between said nonwoven web and said three-dimensional absorbent material.

Use of the term "substrate" includes, but is not limited to, woven or nonwoven webs, porous films, ink permeable films, paper, composite structures, or the like.

Superabsorbent materials suitable for use in the present disclosure are known to those skilled in the art, and may be in any operative form, such as particulate form, fibers and mixtures thereof. Generally stated, the "superabsorbent material" can be a water-swellable, generally water-insoluble, hydrogel-forming polymeric absorbent material, which is capable of absorbing at least about 15, suitably about 30, and possibly about 60 times or more its weight in physiological saline (e.g. saline with 0.9 wt % NaCl). The superabsorbent material may be biodegradable or bipolar. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers may be lightly crosslinked to render the material substantially water insoluble. Crosslinking may, for example, be by irradiation or covalent, ionic, Van der Waals, or hydrogen bonding. The superabsorbent material may suitably be included in an appointed storage or retention portion of the absorbent system, and may optionally be employed in other components or portions of the absorbent article. The superabsorbent material may be included in the absorbent layer or other fluid storage layer of the absorbent article of the present disclosure in an amount up to about 60% by weight. Typically, the superabsorbent material, when present, will be included in an amount of about 5% to about 40% by weight, based on the total weight of the absorbent layer.

"Superabsorbent polymer particles" or "SAPs" refer to water-swellable, water-insoluble organic or inorganic materials capable, under the most favorable conditions, of absorbing at least about 10 times their weight, or at least about 15 times their weight, or at least about 25 times their weight in an aqueous solution containing 0.9 weight percent sodium chloride. In absorbent articles, such as diapers, incontinent diapers, etc., the particle size is typically ranging between 100 to 800 µm, preferably between 300 to 600 µm, more preferably between 400 to 500 µm.

The term "target zone" refers to an area of an absorbent core where it is particularly desirable for the majority of a fluid insult, such as urine, menses, or bowel movement, to initially contact. In particular, for an absorbent core with one or more fluid insult points in use, the insult target zone refers to the area of the absorbent core extending a distance equal to 15% of the total length of the composite from each insult point in both directions.

"Tension" includes a uniaxial force tending to cause the extension of a body or the balancing force within that body resisting the extension.

As used herein, the term "thermoplastic" is meant to describe a material that softens when exposed to heat and which substantially returns to its original condition when cooled to room temperature.

The term "top sheet" refers to a liquid permeable material sheet forming the inner cover of the absorbent article and which in use is placed in direct contact with the skin of the wearer. The top sheet is typically employed to help isolate the wearer's skin from liquids held in the absorbent structure. The top sheet can comprise a nonwoven material, e.g. spunbond, meltblown, carded, hydroentangled, wetlaid etc. Suitable nonwoven materials can be composed of man-made fibres, such as polyester, polyethylene, polypropylene, viscose, rayon etc. or natural fibers, such as wood pulp or cotton fibres, or from a mixture of natural and man-made fibres. The top sheet material may further be composed of two fibres, which may be bonded to each other in a bonding pattern. Further examples of top sheet materials are porous foams, apertured plastic films, laminates of nonwoven materials and apertured plastic films etc. The materials suited as top sheet materials should be soft and non-irritating to the skin and be readily penetrated by body fluid, e.g. urine or menstrual fluid. The inner coversheet may further be different in different parts of the absorbent article. The top sheet fabrics may be composed of a substantially hydrophobic material, and the hydrophobic material may optionally be treated with a surfactant or otherwise processed to impart a desired level of wettability and hydrophilicity.

"Training pants" are available for use by children in the potty-training stage, and are popular with mothers and caretakers. A training pant typically comprises a top sheet, a back sheet, an absorbent medium between the top sheet and the back sheet, and side seams that bond portions of the side edges of the pant together to form waist and leg openings.

As used herein, the term "transverse" or "lateral" refers to a line, axis, or direction which lies within the plane of the absorbent article and is generally perpendicular to the longitudinal direction.

"Ultrasonic welding" refers to a technology which joins two materials by melting them with heat generated from ultrasonic oscillation and then laminating them together, such that the molten materials flow and fill the gap between the two unaffected portions of the two materials, respectively. Upon cooling and shaping, the two materials are joined together.

As used herein, the term "water-swellable, water-insoluble" is meant to refer to a material that, when exposed to an excess of water, swells to its equilibrium volume but does not dissolve into the solution. As such, a water-swellable, water-insoluble material generally retains its original identity or physical structure, but in a highly expanded state, during the absorption of the water and, thus, must have sufficient physical integrity to resist flow and fusion with neighboring particles.

By the term "wrapping material" as used herein, is meant a bendable material, preferably a sheet material of which the thickness is smaller, more preferably much smaller than its width or length, such as a sheet, a film or a foil. In a particularly preferred embodiment, said wrapping material is capable of being rolled up.

Due to the high concentrations of superabsorbent particles, or other high-absorbency material, in the retention portion, there can be an increased difficulty with regard to containing the high-absorbency particles within the retention portion and restricting the movement or migration of the superabsorbent onto the bodyside of the diaper. To improve the containment of the high-absorbency material, the absorbent structure can include an improved overwrap, such as a "wrap sheet", placed immediately adjacent and around the retention portion. The wrap sheet is preferably a layer of absorbent material which covers the major bodyside and outerside surfaces of the retention portion, and preferably encloses substantially all of the peripheral edges of the retention portion to form a substantially complete envelope thereabout. Alternatively, the wrap sheet can provide an absorbent wrap which covers the major bodyside and outerside surfaces of the retention portion, and encloses substantially only the lateral side edges of the retention portion. Accordingly, both the linear and the inwardly curved portions of the lateral side edges of the wrap sheet would be closed about the retention portion. In such an arrangement, however, the end edges of the wrap sheet may not be completely closed around the end edges of the retention portion at the waistband regions of the article. The wrap sheet may comprise a multi-element wrapsheet which includes a separate bodyside wrap layer and a separate outerside wrap layer, each of which extends past all or some of the peripheral edges of the retention portion. Such a configuration of the wrap sheet can, for example, facilitate the formation of a substantially complete sealing and closure around the peripheral edges of the retention portion. The bodyside and outerside layers of the wrap sheet may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials (for example may comprise a meltblown web composed of meltblown polypropylene fibers or low porosity cellulosic tissue web composed of a blend of hardwood/softwood fibers) which has a relatively low porosity. The low porosity bodyside layer can better prevent the migration of superabsorbent particles onto the wearer's skin, and the high porosity, lower basis weight outerside layer can help reduce costs.

Embodiments of the articles and processes according to the disclosure will now be described. It is understood that technical features described in one or more embodiments may be combined with one or more other embodiments without departing from the intention of the disclosure and without generalization therefrom.

Absorbent Core

Absorbent cores 101 according to the present disclosure comprise: a front portion 122; a back portion 124; a crotch portion 126 position between the front portion 122 and the back portion 124; and a longitudinal axis extending along a length of said core 101 and crossing said front, crotch and back portions 122, 126, 124, the absorbent core 101 having a width extending perpendicular to said length and a perimeter comprising at least two opposing ends 102, 103 and at least two opposing sides 104, 105 positioned between said ends 102, 103 wherein the absorbent core 101 comprises one or more substantially interconnected channels 106 extending through at least a portion of the crotch portion 126 (preferably being at least 60%, more preferably at least 70%, even more preferably at least 80%, of a crotch portion length running substantially parallel to the longitudinal axis) along the length of the core and along at least a portion of said width of the core, typically along and substantially parallel to the longitudinal axis, and from one side of the core [e.g. a first side 104] to the other [e.g. a second side 105], preferably said one or more substantially interconnected channels 106 being symmetric or asymmetric about the longitudinal axis. An advantage of such interconnected channel arrangement is that faster immediate distribution of fluid is achieved across the core versus a core free of such interconnected channels or cores comprising only discontinuous channels. Such contributes to limit over-saturation of the core in the portion of fluid discharge. Without wishing to be bound by theory it is believed that the fact that the fluid is distributed across the core and immediately away from the fluid discharge position, a perception of dryness and skin comfort is provided to the subject, as well as an impression of longer lasting dryness by the user.

Figure 11:
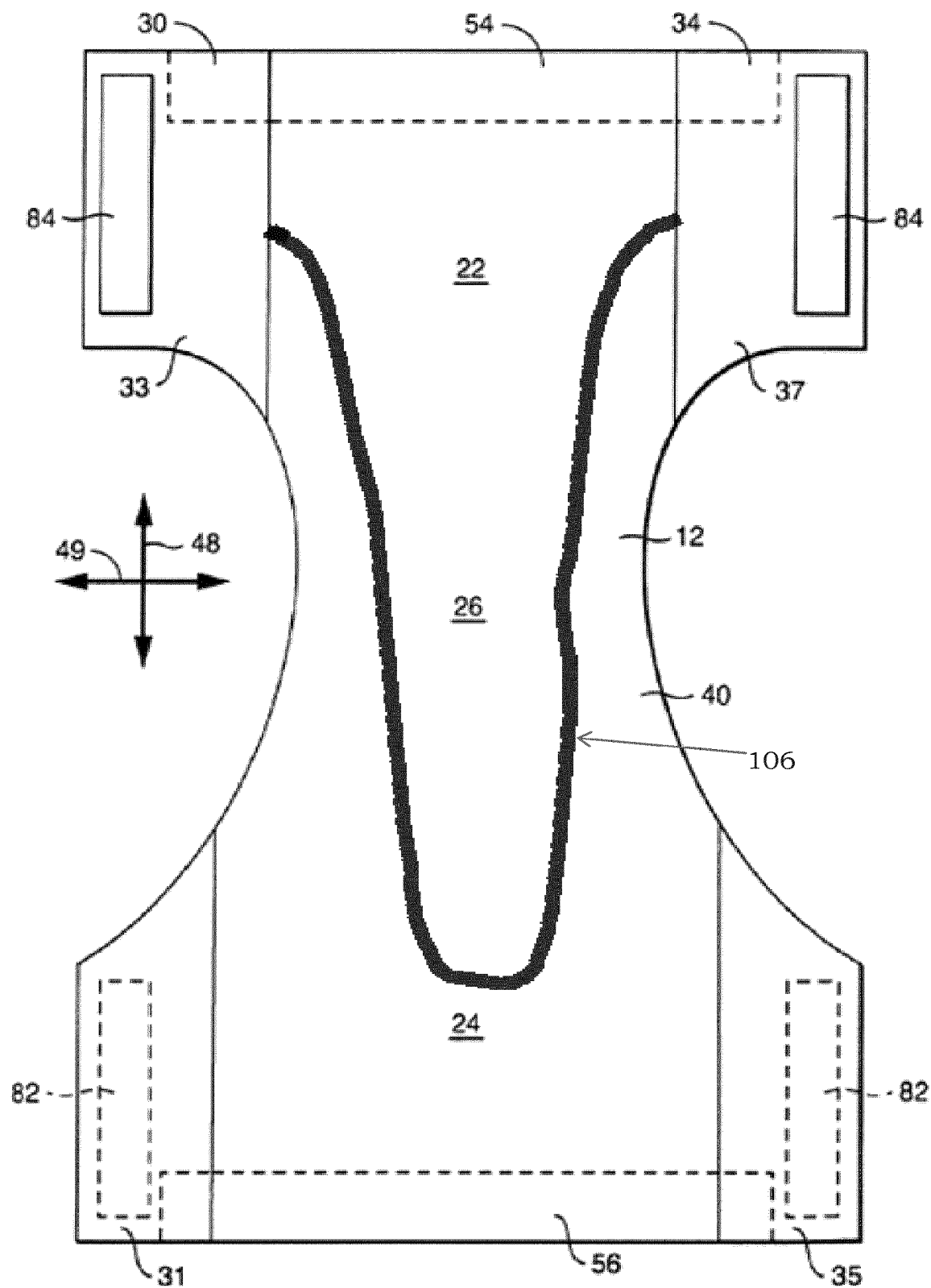
FIG. 11 shows a plan view of an absorbent article according to an embodiment herein.
Figure 12:
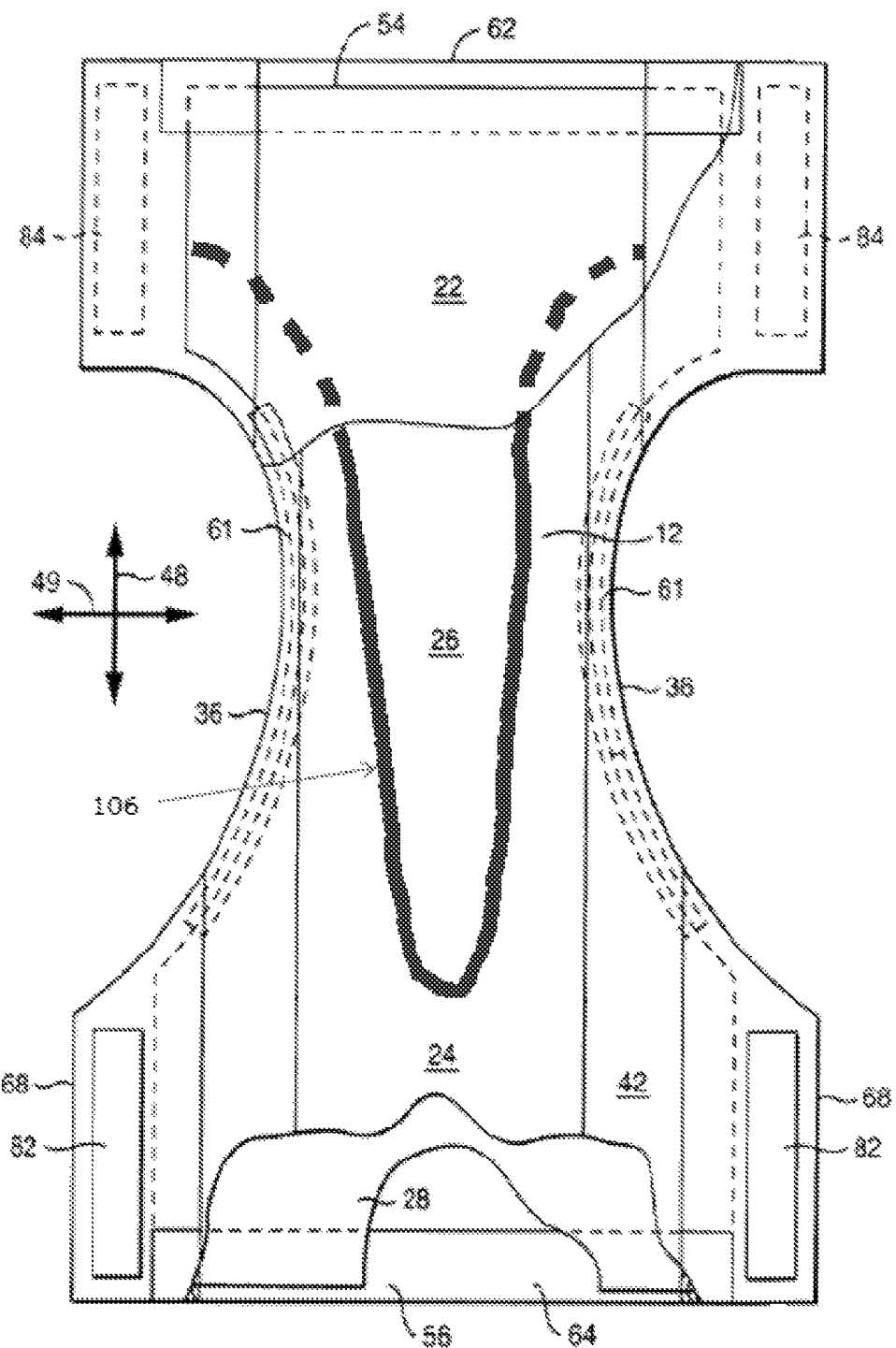
FIG. 12 shows a plan view of an absorbent article according to an embodiment herein.

The longitudinal axis of the core referred to herein may be substantially parallel to the longitudinal direction 48 (as illustrated for example in FIG. 11 and FIG. 12), and the width of the core or width axis of the core referred to herein may be substantially parallel to the lateral direction 49 (as illustrated for example in FIG. 11 and FIG. 12).

In an embodiment the one or more interconnected channels are shaped such to effectively conduct fluid away from a region of discharge, typically by forming a shape that has a distance gradient between opposing surfaces of the interconnected channels, preferably forming a funnel-shaped profile.

Figure 4:
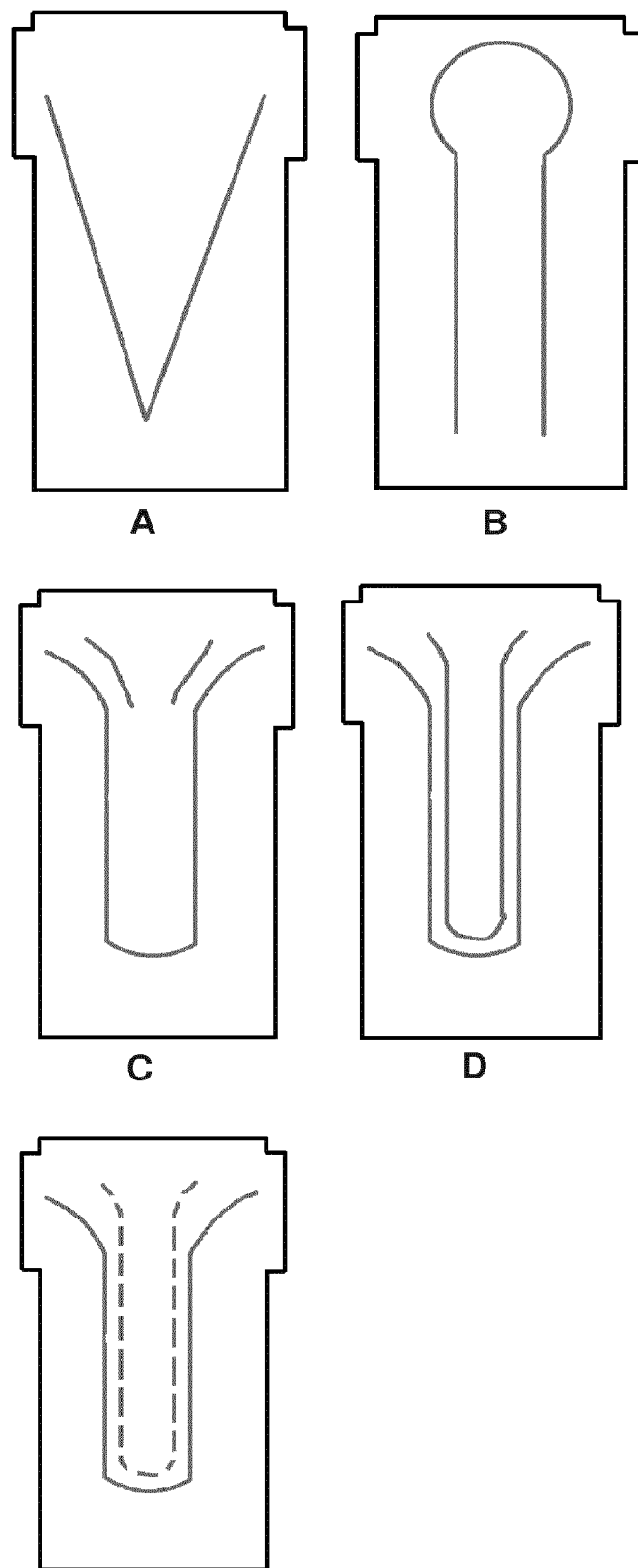
FIG. 4 shows a diagrammatic top view of absorbent cores according to an embodiment herein and having different geometrical shapes formed by interconnected channels.

In an embodiment, the channels form a geometric shape across the absorbent core and along a plane extending parallel to the longitudinal axis of said core, said geometric shape being selected from the group consisting of a semi-hourglass-shaped, v-shaped, u-shaped, pie-shaped, and combinations thereof. Wherein "by semi-hourglass-shaped" it is intended an hourglass shape with only a single end, exemplary shapes are shown in FIG. 4.

In an embodiment, the channels comprise, preferably consist of, a first nonwoven web bonded to a second nonwoven web by one or more adhesives. Preferably, the adhesive is applied in zones across the width of the channels such to form zones, preferably alternating zones, of different bonding strength between the nonwoven web laminate. For example the first nonwoven web may be bonded to the second nonwoven web on at least three zones along the width of the channel. Such arrangement may comprise a first adhesive zone, a second adhesive zone and a third adhesive zone, the second adhesive zone being interposed between the first and third adhesive zones along the width of the channel (e.g. at an axis parallel to the core width and perpendicular to the longitudinal axis of the core) wherein the bonding strength of the second adhesive zone is greater than the bonding strength of the first and third adhesive zones. Examples of ways to achieve such stronger bonding strength in the second zone include using higher amounts of adhesive in this zone, applying greater mechanical pressure on this zone, or utilizing a different adhesive type, other ways are also contemplated provided a stronger adhesion between nonwoven webs results in such region.

In an embodiment the bonding strength in the first and third zones is less than the tensile force generated by the absorbent material located proximal to the channel upon wetting, such that the first and second nonwoven webs may separate in said zones; and wherein the bonding strength in the second zone is greater than the tensile force generated by the absorbent material located proximal to the channel upon wetting, such that the first and second nonwoven webs may not separate in said zone upon wetting and typically the swelling of the absorbent material, and rather may remain fixedly joined. An advantage of this arrangement is that in dry conditions a noticeable channel is visible from the topsheet side of the article and/or core providing broad channels that are further useful for channeling more fluid particularly at initial/early discharge. This arrangement then further allows the bonding at the first and third regions to fail upon for example swelling of the SAP such to allow more volume to be available for expansion thereof (and prevent early saturation or non-optimal absorption), with typically the second zone resisting such expansion and thus providing integrity of the channels even in wet state.

In a preferred embodiment the first nonwoven web and/or the second nonwoven web, preferably the second nonwoven web, are elastic nonwovens (e.g. containing an elastic material such as Vistamaxx resin from ExxonMobil, or other suitable polymers capable of imparting elasticity to a nonwoven web). An advantage of this embodiment is that the nonwoven web better and more easily wraps around the 3D insert upon application of a vacuum and permits subsequent joining to the first nonwoven web at a location corresponding to a position of the base of the 3D insert (opposite a protruding apex thereof). This has an advantage of limiting the formation of fluid collection basins or sinks within the channels.

Figure 2:
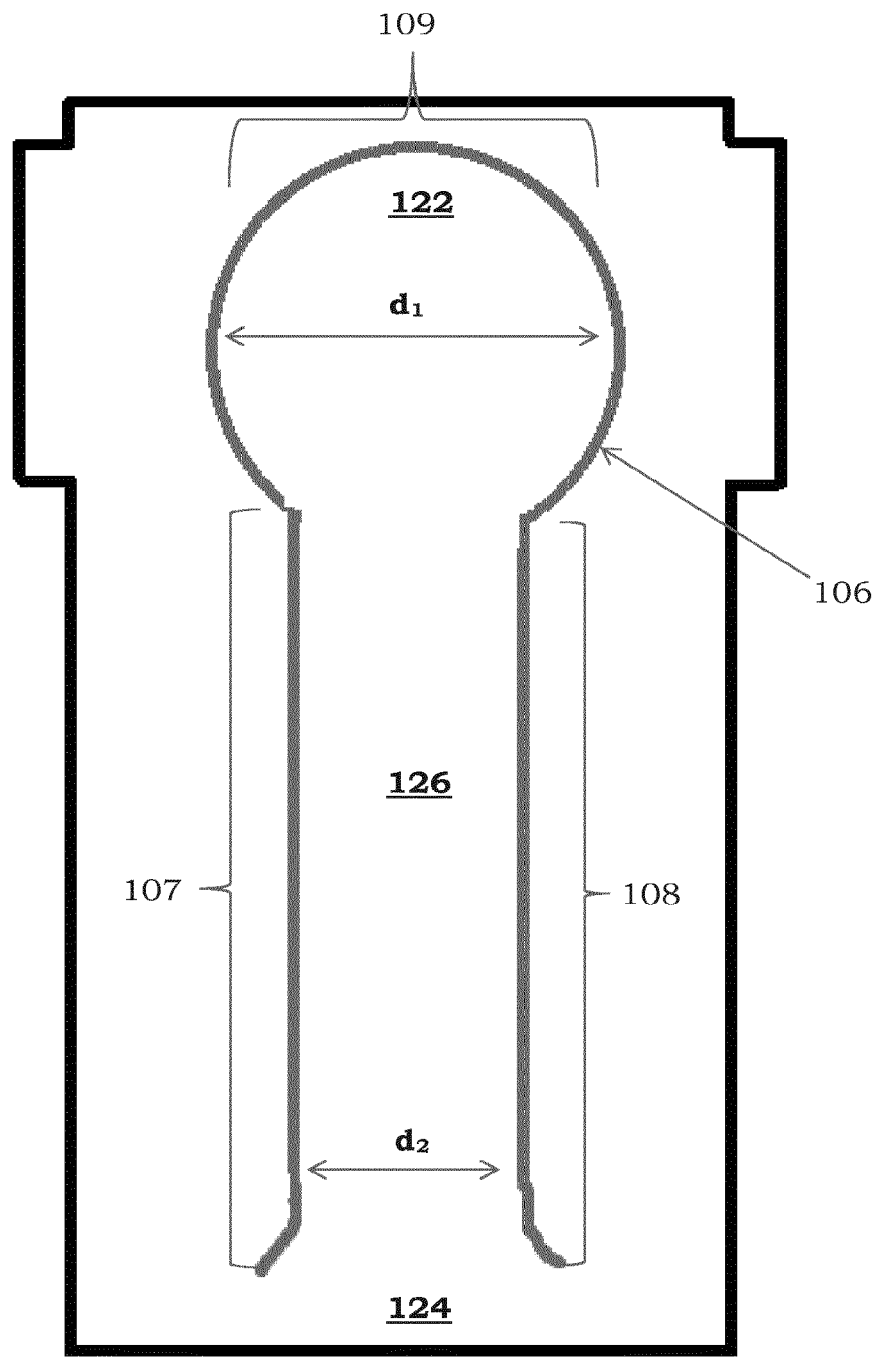
FIG. 2 shows a diagrammatic top view of an absorbent core according to an embodiment herein.
Figure 3:
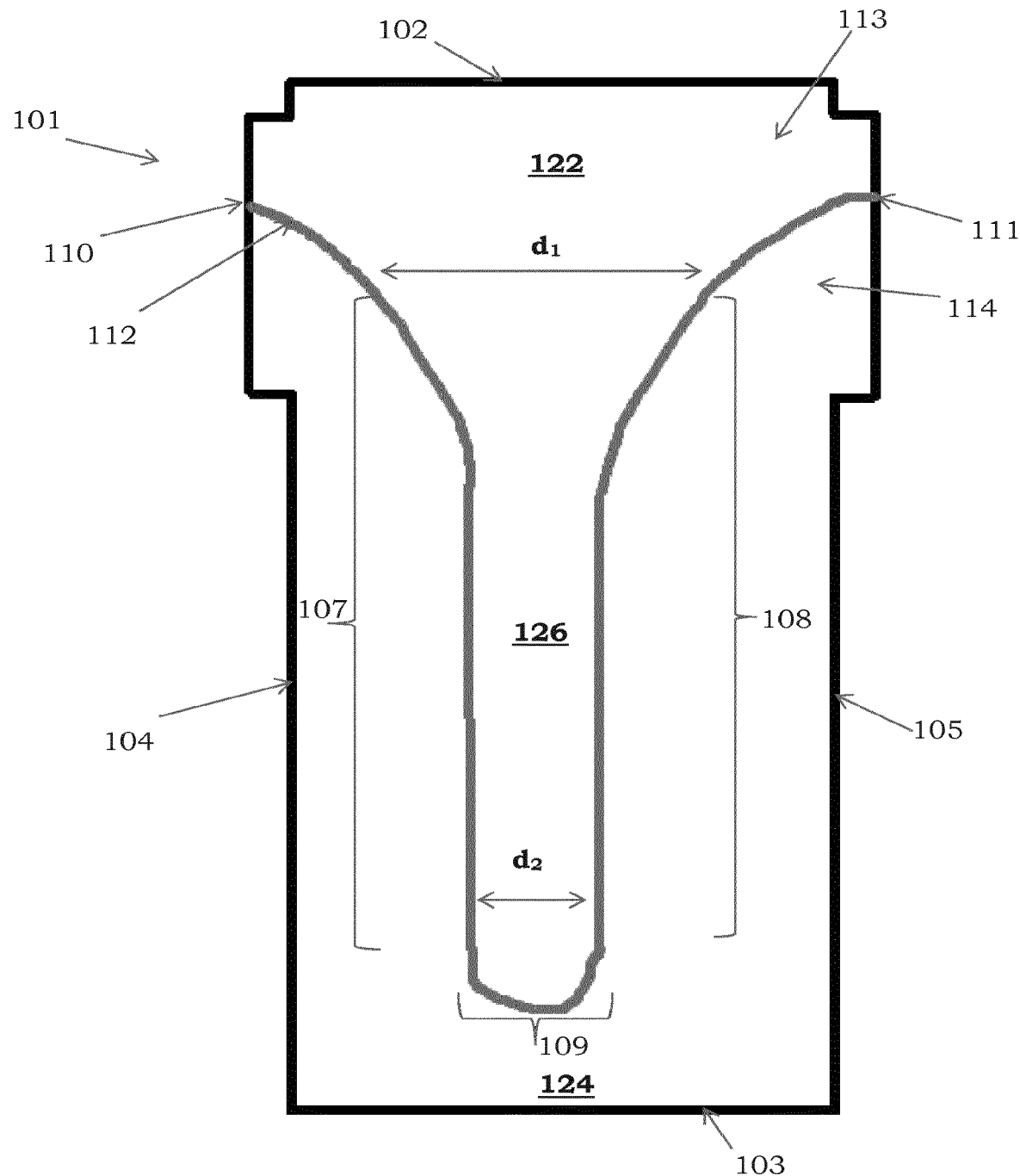
FIG. 3 shows a diagrammatic top view of an absorbent core according to an embodiment herein.

The cores herein may have a substantially rectilinear perimeter such as illustrated in FIG. 1 and FIG. 2, or may comprise symmetrical concave portions in the middle portion thereof as illustrated in FIG. 3. In the latter embodiment, the concave portions may be aligned with and/or positioned in a crotch portion of the absorbent article such to provide better ergonomics and fit along the leg of a wearer. In any of these core shape embodiments, it is preferred that said cores are symmetric at least about the longitudinal axis thereof. Irrespective of the core geometry, it is understood herein that the same or similar channels as described herein may be interchangeably used.

In an embodiment, referring to FIG. 1 to FIG. 3, at least one and preferably each substantially interconnected channel 106 comprises: a first channel portion 107 extending substantially along the longitudinal axis proximal to a first side 104 of the core 101; a second channel portion 108 extending substantially along the longitudinal axis proximal to a second side 105 of the core 101; and at least one, preferably only one, connecting channel portion 109 in fluid communication with said first and second channel portions 107, 108. An advantage of this arrangement is fast liquid distribution along more than one axis of the absorbent core, typically both the longitudinal axis and the width axis thereof, such to maximize the absorption capabilities of the absorbent core over its entire surface area. Moreover, such geometry improves the folding of the core and thus allows for a better and snug fit onto the subjects skin (with or without addition of further elastics proximal to said channel portions).

Hereby, connecting channel portion (109) of at least one of the interconnected channels, the connecting channel portion being in fluid communication with said first and second channel portions (107, 108), preferably forms said closed end in the form of a U-bend, preferably wherein the first and second channel portions (107, 108) diverge away from the longitudinal axis at least along a portion of the interconnecting channel (106) typically exiting from the U-bend, thereby at least partially forming a funnel-shaped interconnected channel near the closed end.

The first and second channel portions may be substantially linear; or have a substantially curved profile preferably selected from concave or convex; or may comprise a combination of said linear and curved profiles. In a preferred embodiment, the first and second channel portions are concave in shape and are generally symmetric about at least the longitudinal axis.

The first and second channel portions may extend through at least a majority, preferably the entirety, of the length of the crotch portion along the longitudinal axis and typically run substantially parallel to the sides of the core forming the perimeter thereof.

In a highly preferred embodiment, each interconnected channel herein comprises only a single connecting channel portion 109, typically forming an apex of the inter connected channel. An advantage of this embodiment is fast fluid distribution through the core whilst limiting the risk of blockages that could otherwise result if pockets of wetted areas are rather formed.

Preferably, the connecting channel portion 109 extends substantially along the width of said core 101, preferably forming a closed end within a surface of said core 101 along a plane parallel to the longitudinal axis, and preferably positioned opposite to an open end formed by non-connected first and second terminal positions 110, 111 of the interconnected channel 106, preferably of the first and second channel portions 107, 108 respectively, typically said non-connected first and second terminal positions 110, 111 being distal to each other and proximal to the first and second sides 104, 105 of said core 101 respectively, even more preferably said terminal positions 110, 111 facing away from each other such to form a funnel-shaped geometrical opening therebetween. Without wishing to be bound by theory it is believed that such geometry aids to "funnel" and collect more fluid where it is needed and quickly and effectively distribute it away from the region of collection.

In an embodiment, and preferably in combination with the previous embodiment, the interconnected channel comprises unconnected first (110) and second (111) terminal positions, whereby the first terminal position (110) extends to a first side (104) of the core and/or the second terminal position (111) extends to a second side (105) of the core, as for instance illustrated in FIG. 3. Hereby the entire width of the absorbent core can be covered by the channel, which ensures a better fluid distribution.

In an embodiment, the closed end is substantially curvilinear in shape, preferably forming a convex shape between the first and second channel portions 107, 108, or is substantially linear in shape, preferably forming a straight or triangular shape between the first and second channel portions 107, 108. The closed end may be formed by the connecting channel portion 109. An advantage of such shape is increasing the surface area of contact with neighboring regions of three-dimensional absorbent material such to better promote absorption of the distributed liquid once evacuated from areas of typically high saturation.

In an embodiment, a first distance ($d_1$) between the first channel portion 107 and the second channel portion 108, a second distance ($d_2$) between the first channel portion 107 and the second channel portion 108, wherein the first distance ($d_1$) is proximal to the front portion 122 of the core 101 and the second distance ($d_2$) is proximal to the back portion 124 of the absorbent core 101, and wherein the first distance ($d_1$) is greater than the second distance ($d_2$), preferably wherein the first distance ($d_1$) is at least 1.5 $d_2$, more preferably from 1.8 $d_2$ to 3 $d_2$. An advantage being the fast and effective fluid distribution from regions of typically high saturation towards regions of typically lower saturation.

In an embodiment, the core comprises a first nonwoven web, typically in the form of a backsheet; a second nonwoven web, typically in the form of a topsheet; and a three-dimensional absorbent material positioned between the first and second nonwoven webs to form an absorbent core laminate, typically wherein the three-dimensional absorbent material comprises a fibrous web typically comprising airlaid fibers, and preferably comprises a predetermined amount of super absorbent polymer dispersed therethrough.

In a highly preferred embodiment, the interconnected channel 106 is substantially free of three-dimensional absorbent material, and preferably also free of super absorbent polymer. Without wishing to be bound by theory it is believed that absorbent materials delay fluid distribution compared to the effectiveness of such channels, indeed as fluid is absorbed by the absorbent materials they swell and/or saturate effectively reducing the amount of fluid that could be allowed to travel therethrough. Eliminating such materials from the channels allows to maintain a highly efficient fluid distribution system that operates substantially independently from the fluid acquisition/absorption mechanism of the neighboring regions.

In a preferred embodiment, the core comprises a plurality of substantially interconnected channels, preferably arranged in a substantially concentric manner, an example being shown in FIG. 4E. An advantage being the exponential effectiveness in liquid distribution and channel formation, particularly as neighboring regions become more saturated or swell.

In an embodiment, as shown in FIGS. 4C and 4D, the core further comprises one or more disconnected channels, preferably at least a portion thereof being arranged concentrically to the substantially interconnected channel. An advantage being effective added local uniform fluid distribution. Moreover, it is believed that upon swelling of the neighboring regions to the channels, upon saturation, visual patterns may be formed that more evidently convey the perception of efficacy of the entire core surface for absorption of fluid.

Preferably, the substantially interconnected channels 106 have a regular or irregular depth, said depth being measured on an axis perpendicular to both the longitudinal axis and the axis along the width of the core 101, preferably wherein the cross-section of said channels 106 is selected from the group consisting of curved, polygonal or combinations thereof.

Figure 16:
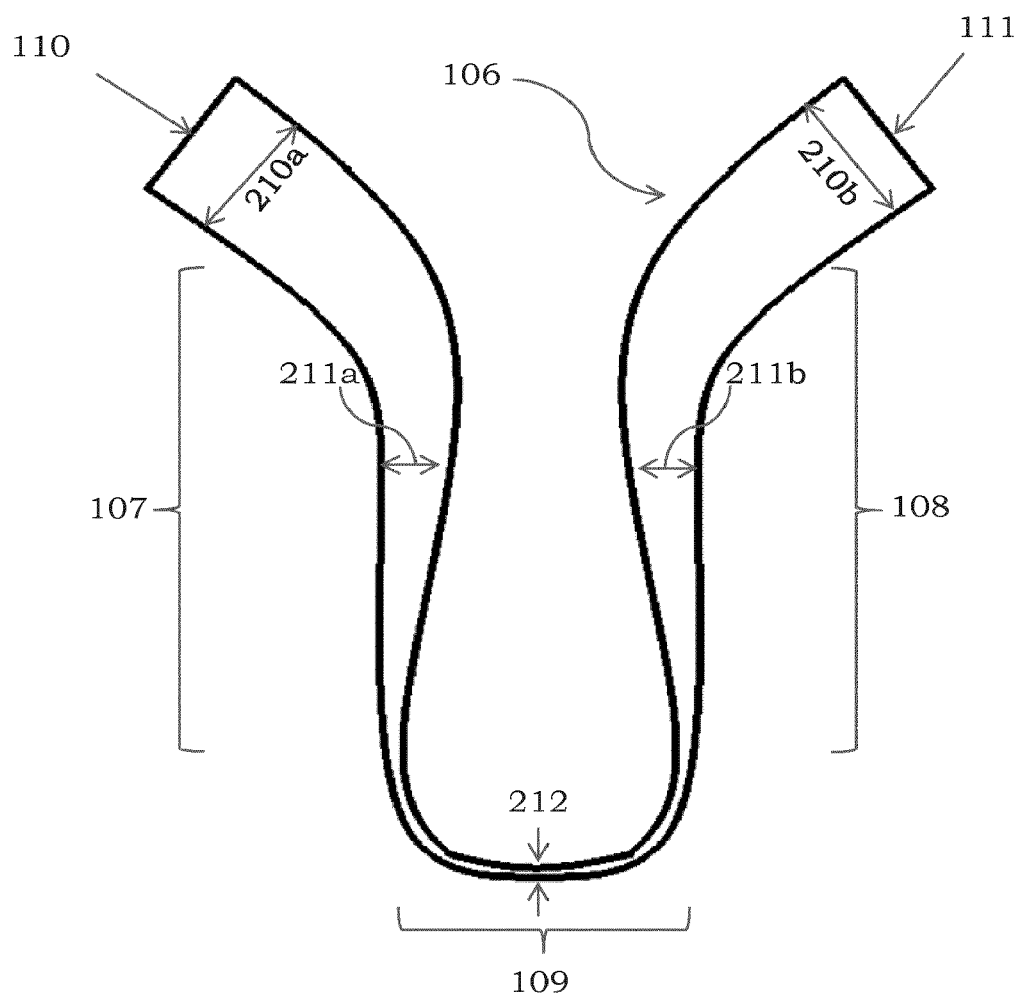
FIG. 16 illustrates interconnected channels wherein the width varies along the channels.

In a preferred embodiment, as illustrated in FIG. 16, the width of the interconnected channel (106) may vary along the channel. Preferably, the width of the channel decreases from the terminal positions (110, 111) towards the connecting channel portion (109). This is illustrated in FIG. 16, wherein the width (210a) of the channel (106) near the first terminal position (110) and the width (210b) of the channel (106) near the second terminal position (111) are larger than the width (211a) of the channel (106) in the first channel portion (107) and the width (211b) of the channel (106) in the second channel portion (108), which are larger than the width (212) of the channel (106) in the connecting channel portion (109). Such variance of the width of the channel portions leads to faster distribution. Without wishing to be bound by theory, the inventors believe that the varying width leverages capillary effects that better promote liquid transport from the front to the back of the absorbent article.

It is understood that a number of alternative shapes may be used for channels described herein, examples of which are shown in FIG. 4 and FIG. 16 without departing from the disclosure embodiments described herein.

The present disclosure further relates to an absorbent core 101 comprising substantially continuous zones of one or more high fluid distribution structures 112 and continuous or discontinuous zones of fluid absorption structures 113, 114 surrounding the one or more high fluid distribution structures 112, wherein the one or more high fluid distribution structures 112 are arranged to distribute fluid across the absorbent core 101 at a speed that is faster than the speed of fluid distribution across the absorbent core by said discontinuous fluid absorption structures 113, 114, and wherein said continuous zones extend along a path that is substantially parallel to at least a portion of the perimeter of the core 101, said portion of the perimeter of the core comprising at least a portion of the sides 104, 105, preferably at least a portion of both of the sides 104, 105, of the core 101 and one of the ends 102, 103 of the core 101 (preferably only one end 103), preferably the end 103 proximal to the back portion 124. Advantages of this embodiment includes separating absorbent regions of the core with fluid distribution regions that effectively uniformly distribute fluid across the core surface with a mechanism as described above as well as providing a visual perception of efficacy.

In an embodiment the fluid distribution structures are shaped such to effectively conduct fluid away from a region of discharge, typically by forming a shape that has a distance gradient between opposing surfaces of said structures, preferably forming a funnel-shaped profile substantially delimited by one or more fluid absorption structures.

In an embodiment, the high fluid distribution structures form a geometric shape across the absorbent core and along a plane extending parallel to the longitudinal axis of said core, said geometric shape being selected from the group consisting of a semi-hourglass-shaped, v-shaped, u-shaped, pie-shaped, and combinations thereof. Wherein "by semi-hourglass-shaped" it is intended an hourglass shape with only a single end as for example shown in FIG. 4B.

In a preferred embodiment, the one or more high fluid distribution structures comprise, preferably consist of, at least two nonwoven webs bonded together (for example with an adhesive); and the zones of fluid absorption structures comprise a three-dimensional absorbent material (such as cellulosic fluff and/or fibrous web typically comprising airlaid fibers, typically of the cellulosic kind) and/or a superabsorbent polymer (typically in the form of a plurality of discrete particles that may be distributed within the three-dimensional absorbent material or directly agglomerated in one or more pockets between at least two nonwoven webs).

Preferably, said fluid distribution structures comprise substantially interconnected channels as described in the previous embodiments, and the fluid absorption structures comprise a three-dimensional absorbent material and/or superabsorbent polymer as described in the previous embodiments.

Absorbent Articles

In an aspect of the disclosure, an absorbent article comprises a core as described above. Preferably said article being selected from disposable diapers or diaper pants; disposable incontinence diapers or diaper pants; sanitary napkins; or panty liners; and typically wherein the channels in said core remain visible both before and after use of the article, preferably wherein the channels are more visible after use than before use of the article.

In an embodiment, the absorbent article comprises a topsheet and a backsheet enclosing the core, wherein at least one of the backsheet or topsheet comprises a color that is different from the color of the core, preferably wherein the backsheet has a color that is different from the color of the topsheet and core, such that the channels may be visually discernible from the topsheet side of the article.

The Examples herein provide further embodiments and structural technical features that may be included (in isolation or combination) in absorbent articles according to the present disclosure. It is however understood that alternative structural features of the absorbent article may be applied without departing from the inventive scope of the present disclosure.

Acquisition and Distribution Layer

One particular preferred component which can be used in absorbent articles, in combination with the present invention, is an acquisition and distribution layer (ADL). The ADL is hereby positioned at body-facing side of the absorbent core, preferably between a topsheet and the absorbent core of the absorbent article, and more preferably in close proximity or even in good contact with the body-facing side of the absorbent core. The use of an ADL in combination with the fluid distribution structures and/or interconnected channels of the present invention lead to an extremely good distribution of fluids from a discharge area to the entire absorbent core.

The inventors have found that fluid distribution in embodiments of the absorbent article according to the present invention which comprise an ADL, may depend on the relative size and positioning of the ADL with respect to the fluid distribution structure, and in particular the interconnected channels, of the absorbent core.

Figure 17A:
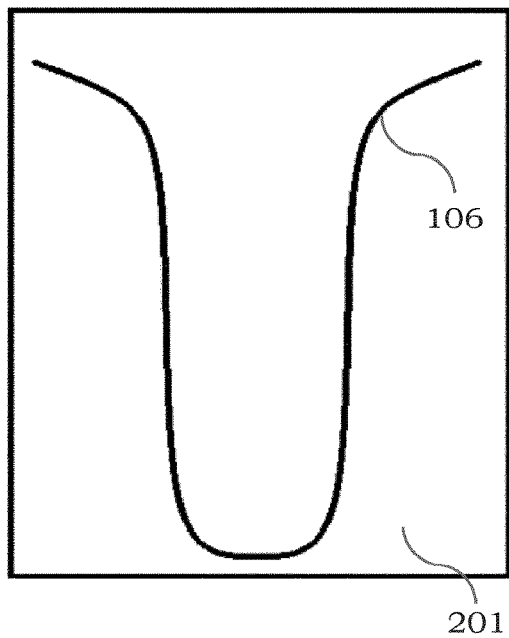
FIGS. 17A-D illustrate embodiments of the present invention wherein the absorbent core is combined with an acquisition and distribution layer.

FIGS. 17A-D illustrate embodiments with an ADL (201) and its relative size and position with respect to interconnected channels (106). FIG. 17A shows an embodiment wherein the ADL (201) covers the full channel (106). Such an arrangement already improves over prior art arrangements because the combined effects of the ADL and interconnected channel lead to a substantial improvement in the distribution of fluids over the complete absorbent core. Nevertheless, the inventors have found that certain arrangements provide even better improvements in the distribution of liquids, these arrangements being illustrated in FIGS. 17B-D and further discussed below.

Figure 17B:
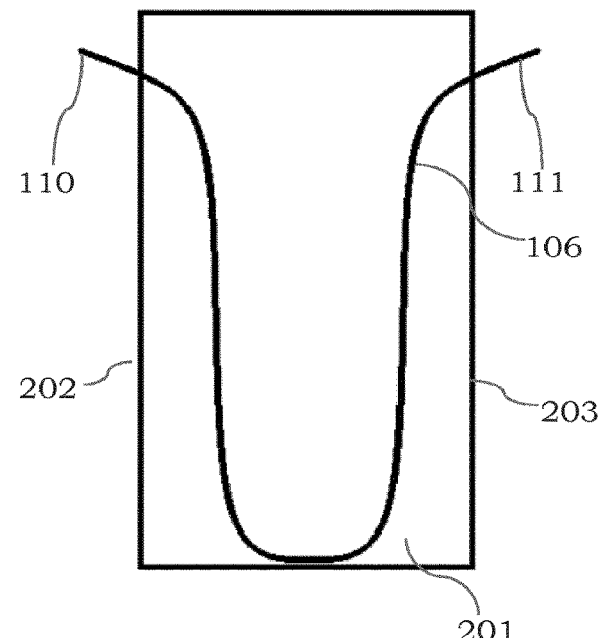

FIG. 17B illustrates a preferred embodiment wherein the ADL (201) is narrower than the interconnected channel (106), and positioned such that the first (110) and second (111) terminal positions extend beyond the side edges (202, 203) of the ADL.

Figure 17C:
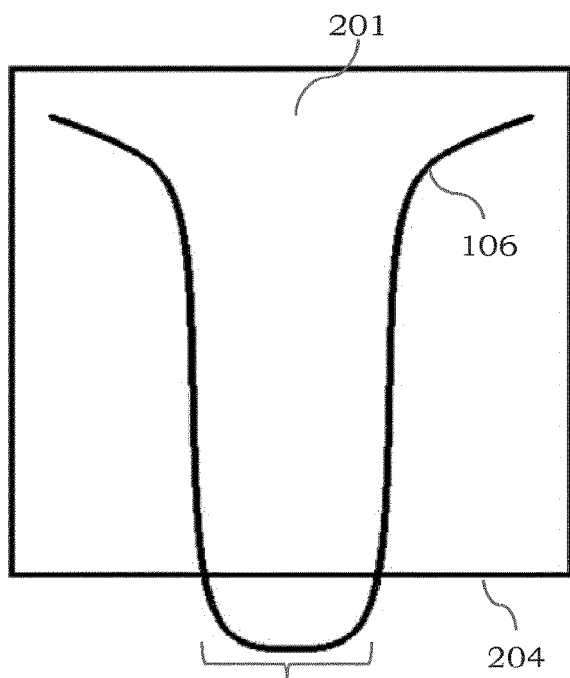

FIG. 17C illustrates a preferred embodiment wherein the ADL (201) is positioned such that the connecting channel portion (109) extends beyond a rear edge (204) of the ADL. The connecting channel portion (109) preferably comprises or has the shape of a U-bend.

Figure 17D:
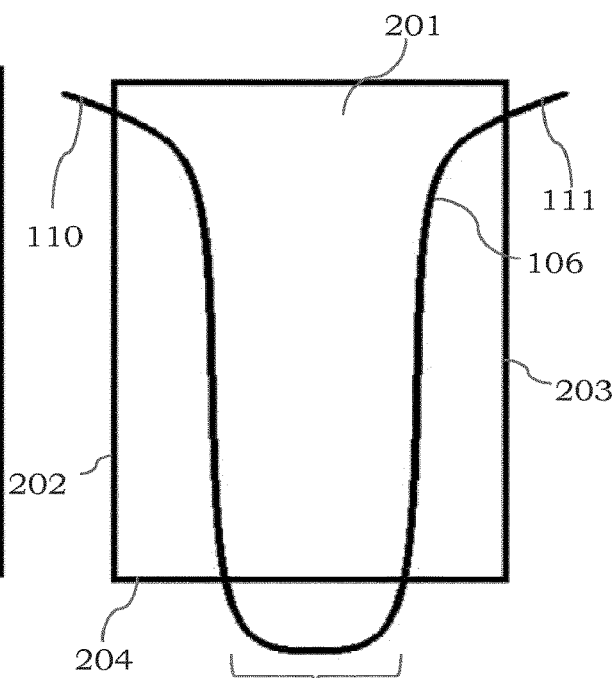

FIG. 17D illustrates a preferred embodiment wherein the ADL (201) is narrower than the interconnected channel (106), and positioned such that the first (110) and second (111) terminal positions extend beyond the side edges (202, 203) of the ADL, and wherein the ADL (201) is positioned such that the connecting channel portion (109) extends beyond a rear edge (204) of the ADL. The connecting channel portion (109) preferably comprises or has the shape of a U-bend.

These arrangements which are illustrated in FIGS. 17B-D, have in common that certain extremities of the interconnected channel (106), in particular the terminal positions (110, 111) and/or the connecting channel portion (109), are not covered by the ADL and thus are more intimately exposed to the wearer. Without wishing to be bound by theory, the inventors believe that these extremities are very beneficial in the working of the interconnected channel (106) in distributing fluids from the discharge area towards regions of the absorbent core which are typically unexposed, or at least not directly exposed, to fluid discharges. By ensuring that the ADL does not cover some or all of these extremities, it is believed that fluid in-flow and/or fluid out-flow for the interconnected channel is maximized. Furthermore, these embodiments allow to use a smaller ADL, and thus less raw material, in the absorbent article.

Methods Of Making and Uses

The disclosure relates to a process of making an absorbent core 101 comprising the steps of:

i. providing a mold comprising a 3D insert therein, said 3D insert being the inverse shape of the desired channels, wherein substantially the entire surface of the mold is in fluid communication with an under-pressure source except for the 3D insert;

ii. applying a first nonwoven web to said mold;

iii. applying a three-dimensional absorbent material over at least a portion of said nonwoven;

iv. applying a second nonwoven web directly or indirectly over the three-dimensional absorbent material;

v. optionally applying a bonding step to form a laminate comprising said first nonwoven, said second nonwoven and said three-dimensional absorbent material therebetween;

vi. optionally removing said laminate from the mold to form an absorbent core comprising channels having the inverse shape of said 3D insert; and wherein at least for the duration of step iii the underpressure source is arranged to provide a vacuum force forcing said three-dimensional absorbent material around the 3D insert such to substantially evacuate the surface thereof from three-dimensional absorbent material and form channels substantially free of three-dimensional absorbent material. Such process has been found effective in creating channels substantially free of three-dimensional absorbent material compared to processes using embossing (i.e. creating channels of highly dense/packed three-dimensional absorbent material) or material removal processes that comprise removing three-dimensional absorbent material from a pre-formed core structure which inevitably results in the presence of some three-dimensional absorbent material that may affect effective/uniform fluid distribution upon saturation thereof.

Figure 15A:
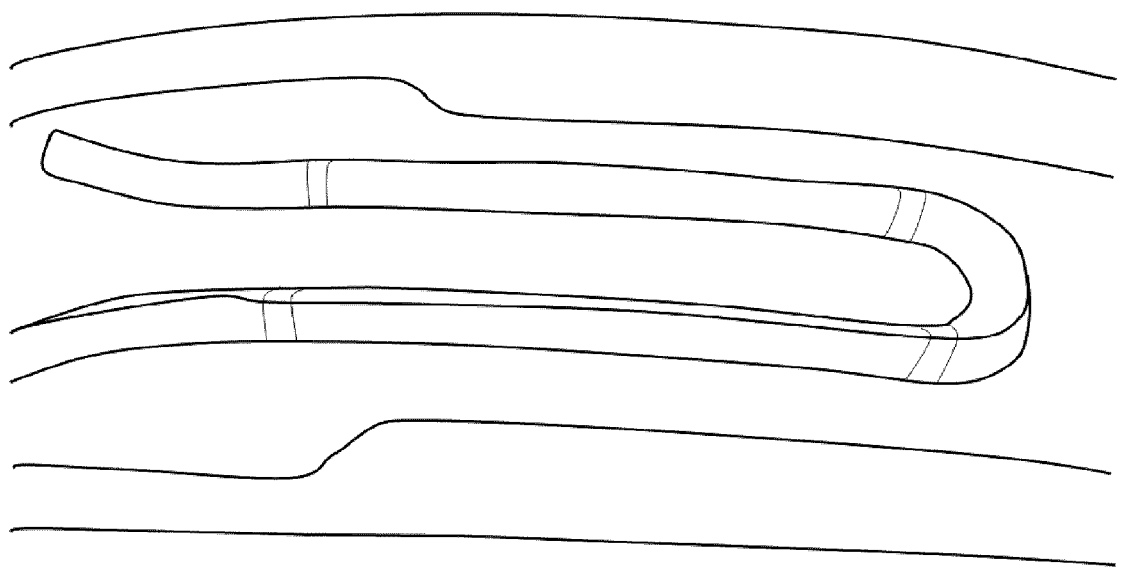
FIG. 15A and FIG. 15B show images of molds comprising a 3D insert according to an aspect of the present disclosure.
Figure 15B:
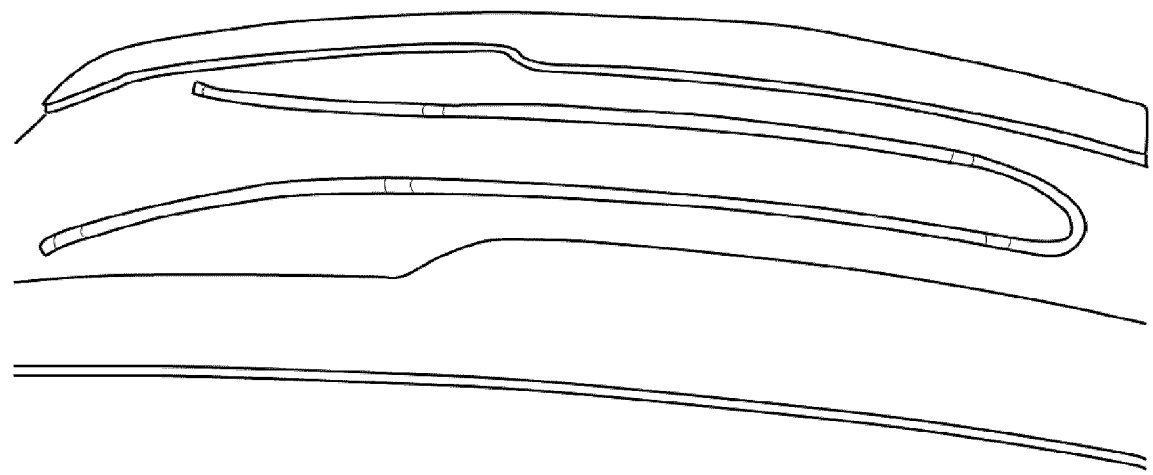

FIG. 15A and FIG. 15B illustrate an example of a mold comprising a 3D insert as described herein.

In an embodiment, the mold comprises a plurality of perforations or openings across its surface typically forming channels arranged to be in fluid (preferably air) communication with the under pressure source. Preferably, the 3D insert is positioned above and/or over said mold surface comprising a plurality of said perforations or openings and said 3D insert being free of said perforations or openings and consists of a solid component that is not in fluid communication with the under pressure source.

Preferably, the 3D insert has a cross-sectional shape selected from the group consisting of square, rectangular, oval, semi-circular, and combinations thereof.

More preferably, the 3D insert has the same or varying depth throughout the perimeter thereof.

In an embodiment, the 3D insert is 3D-printed, preferably made from a material selected from alumide, or is made from metal and formed by milling or casting.

In a preferred embodiment, the bonding step comprises applying an adhesive on a surface of the second nonwoven web and joining said web to said first nonwoven web and/or three-dimensional absorbent material, preferably the adhesive being applied in continuous or discontinuous spaced apart stripes aligned with said channels such that the resulting core laminate comprises adhesive rich and adhesive poor regions, wherein the adhesive rich regions are substantially located along said channels and the adhesive poor regions are located in areas of the core other than said channels. An advantage of this embodiment is to limit the risk of adhering absorbent material within the channels and to rather directly bond the topsheet and backsheet nonwoven together at these channel locations.

In an embodiment, the adhesive is applied in zones across the width of the channels such to form zones, preferably alternating zones, of different bonding strength between the laminate. For example the first nonwoven web may be bonded to the second nonwoven web on at least three zones along the width of the channel. Such arrangement may comprise a first adhesive zone, a second adhesive zone and a third adhesive zone, the second adhesive zone being interposed between the first and third adhesive zones along the width of the channel (e.g. at an axis parallel to the core width and perpendicular to the longitudinal axis of the core) wherein the bonding strength of the second adhesive zone is greater than the bonding strength of the first and third adhesive zones. Examples of ways to achieve such stronger bonding strength in the second zone include using higher amounts of adhesive in this zone, applying greater mechanical pressure on this zone, or utilizing a different adhesive type, other ways are also contemplated provided a stronger adhesion between nonwoven webs results in such region.

In an embodiment the bonding strength in the first and third zones is less than the tensile force generated by the absorbent material located proximal to the channel upon wetting, such that the first and second nonwoven webs may separate in said zones upon wetting; and wherein the bonding strength in the second zone is greater than the tensile force generated by the absorbent material located proximal to the channel upon wetting, such that the first and second nonwoven webs may not separate in said zone upon swelling of the absorbent material and rather may remain fixedly joined. An advantage of this arrangement is that in dry conditions a noticeable channel is visible from the topsheet side of the article and/or core providing broad channels that are further useful for channeling more fluid particularly at initial/early discharge. This arrangement then further allows the bonding at the first and third regions to fail upon for example swelling of the SAP such to allow more volume to be available for expansion thereof (and prevent early saturation or non-optimal absorption), with typically the second zone resisting such expansion and thus providing integrity of the channels even in wet state.

In a preferred embodiment the first nonwoven web and/or the second nonwoven web, preferably the second nonwoven web, are elastic nonwovens (e.g. containing an elastic material such as Vistamaxx resin from ExxonMobil). An advantage of this embodiment is that the nonwoven web better and more easily wraps around the 3D insert upon application of a vacuum and permits subsequent joining to the first nonwoven web at a location corresponding to a position of the base of the 3D insert (opposite a protruding apex thereof). This has an advantage of limiting the formation of fluid collection basins or sinks within the channels.

More preferably, the channels are formed substantially only by said vacuum force and no additional mechanical action such as embossing.

In an embodiment, the adhesive is applied such that, when laminated, the adhered first and second nonwoven webs in the channel locations is substantially flush with the non-adhered portions of the second nonwoven web such to limit the formation of fluid retention pockets in the resulting laminated core. An advantage of this embodiment is to prevent the formation of pockets of fluid that may reduce comfort to the subject.

The mold described herein above may be contained within the circumference of a rotating drum apparatus, said drum apparatus typically comprising a plurality of said molds along its circumference. Said drum apparatus may be integrated within existing apparatuses for forming absorbent core laminates. An advantage of such a simple arrangement is that it allows for the formation of such novel absorbent cores in a simple and effective manner without considerable capital investment to substantially change major parts of existing core forming equipment.

The disclosure also relates to the use of an absorbent core described in the previous sections herein in an absorbent article described above, for improved liquid distribution compared to the same absorbent article comprising a core free of substantially interconnected channels.

The disclosure further relates to the use of an absorbent core described in the previous sections herein in an absorbent article described above, for providing a tri-stage fluid acquisition typically comprising a first fluid distribution at a first speed, a second fluid distribution at a second speed and a third fluid distribution at a third speed, said first speed being greater or equal to said second speed and said third speed being less than said first speed and less than or equal to said second speed, preferably wherein the first fluid distribution is driven by the substantially interconnected channels, the second fluid distribution is driven by a three-dimensional absorbent material comprised within the core, and the third fluid distribution is driven by an amount of super absorbent polymer dispersed within the three-dimensional absorbent material. Without wishing to be bound by theory it is believed that the novel cores described herein comprising the novel interconnected channel arrangement described, allows to achieve a unique and first in kind distinct fluid distribution and absorption system whereby firstly the channels provide for fast liquid distribution/evacuation from the region of discharge, followed by further distribution from neighboring surfaces of the channels towards other portions of the core via the three-dimensional absorbent material, and finally the super absorbent polymer dispersed within the three-dimensional absorbent material when presented with fluid begins an absorption of said fluid whilst swelling such to permit the three-dimensional absorbent material to distribute and transfer more of said fluid to the super absorbent polymer.

The disclosure is further described by the following non-limiting examples which further illustrate the disclosure, and are not intended to, nor should they be interpreted to, limit the scope of the disclosure.

EXAMPLES

Example 1

FIGS. 5-8 representatively illustrate an example of a disposable diaper, as generally indicated at 20, according to the present disclosure.

Figure 5:
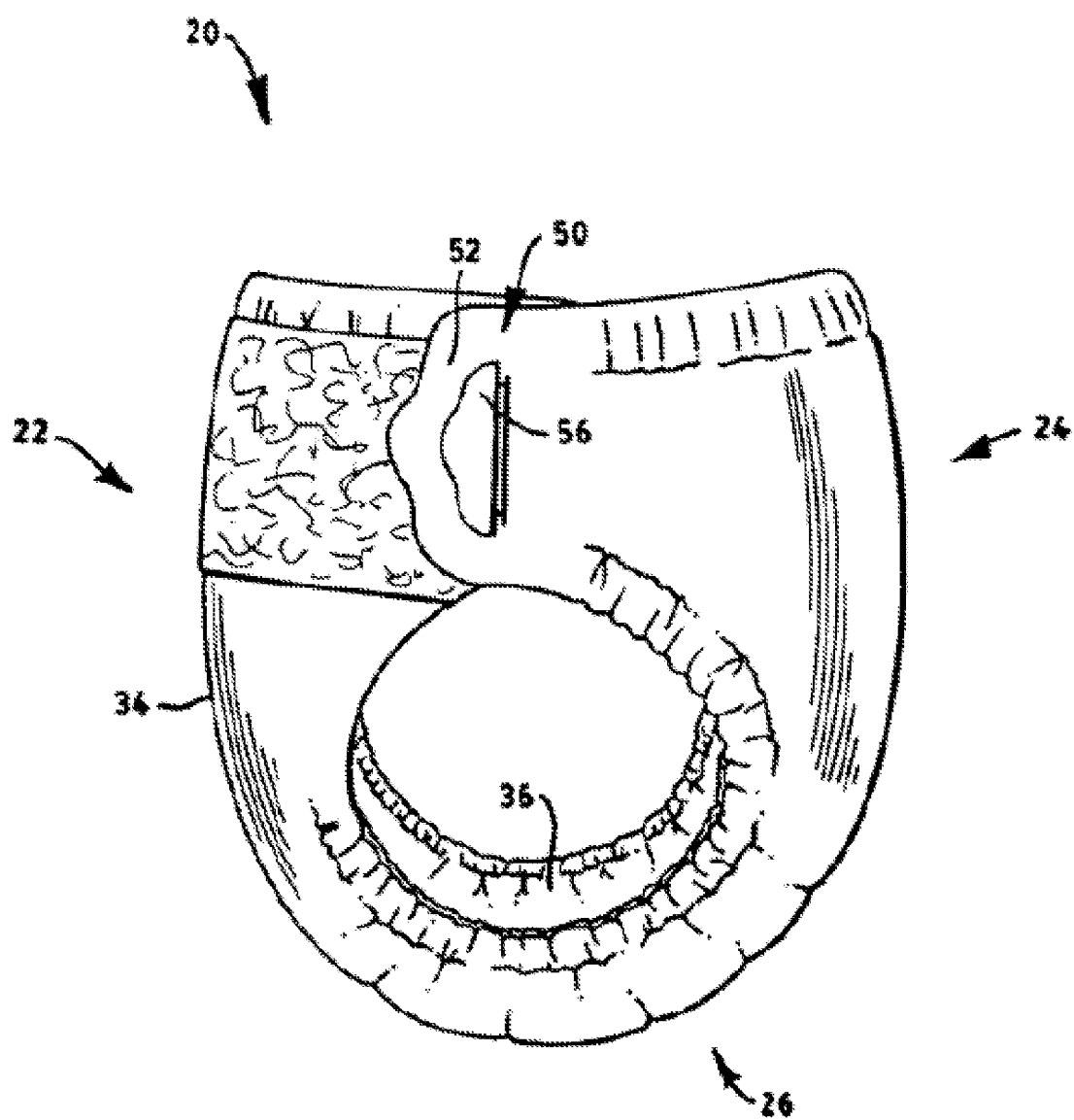
FIG. 5 shows a perspective overview of an absorbent article according to an embodiment herein.
Figure 6:
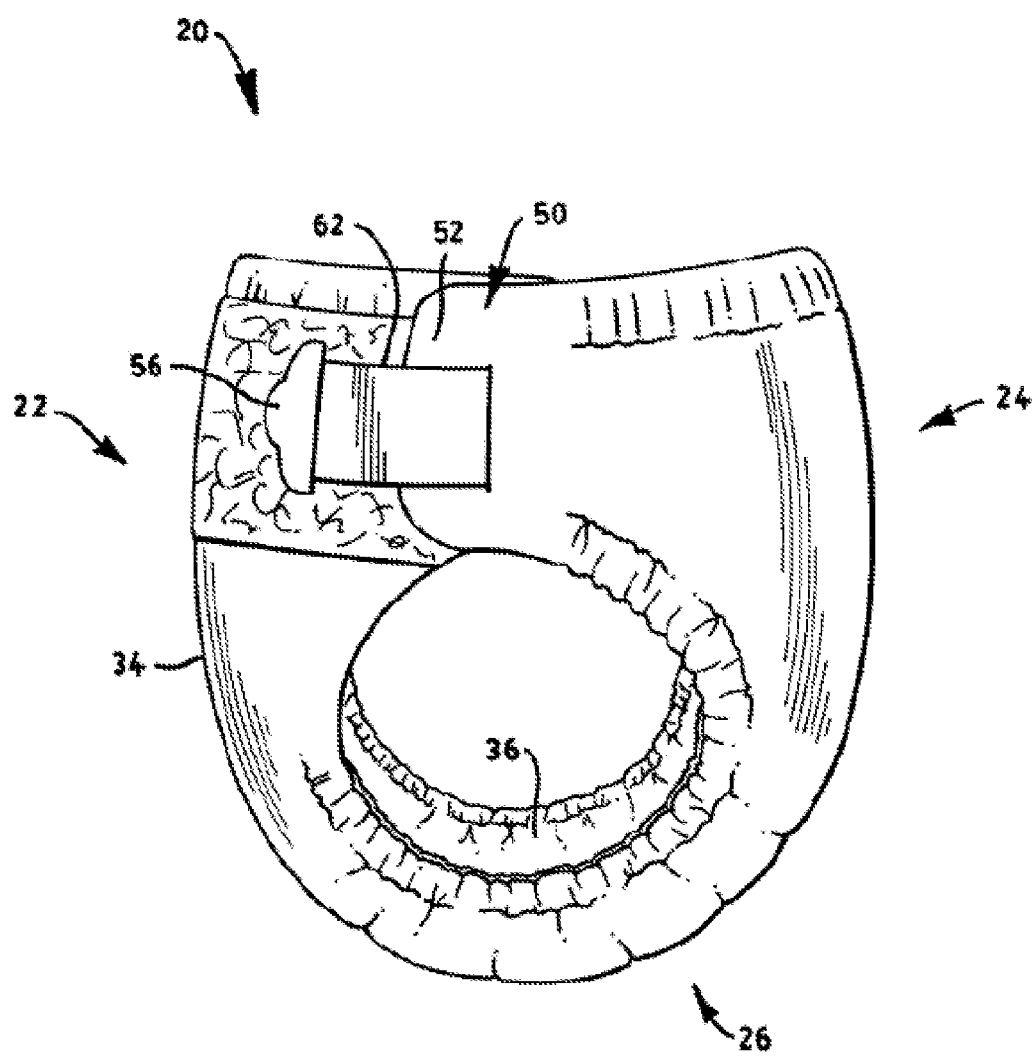
FIG. 6 shows a perspective overview of a product according to an embodiment herein.
Figure 7:
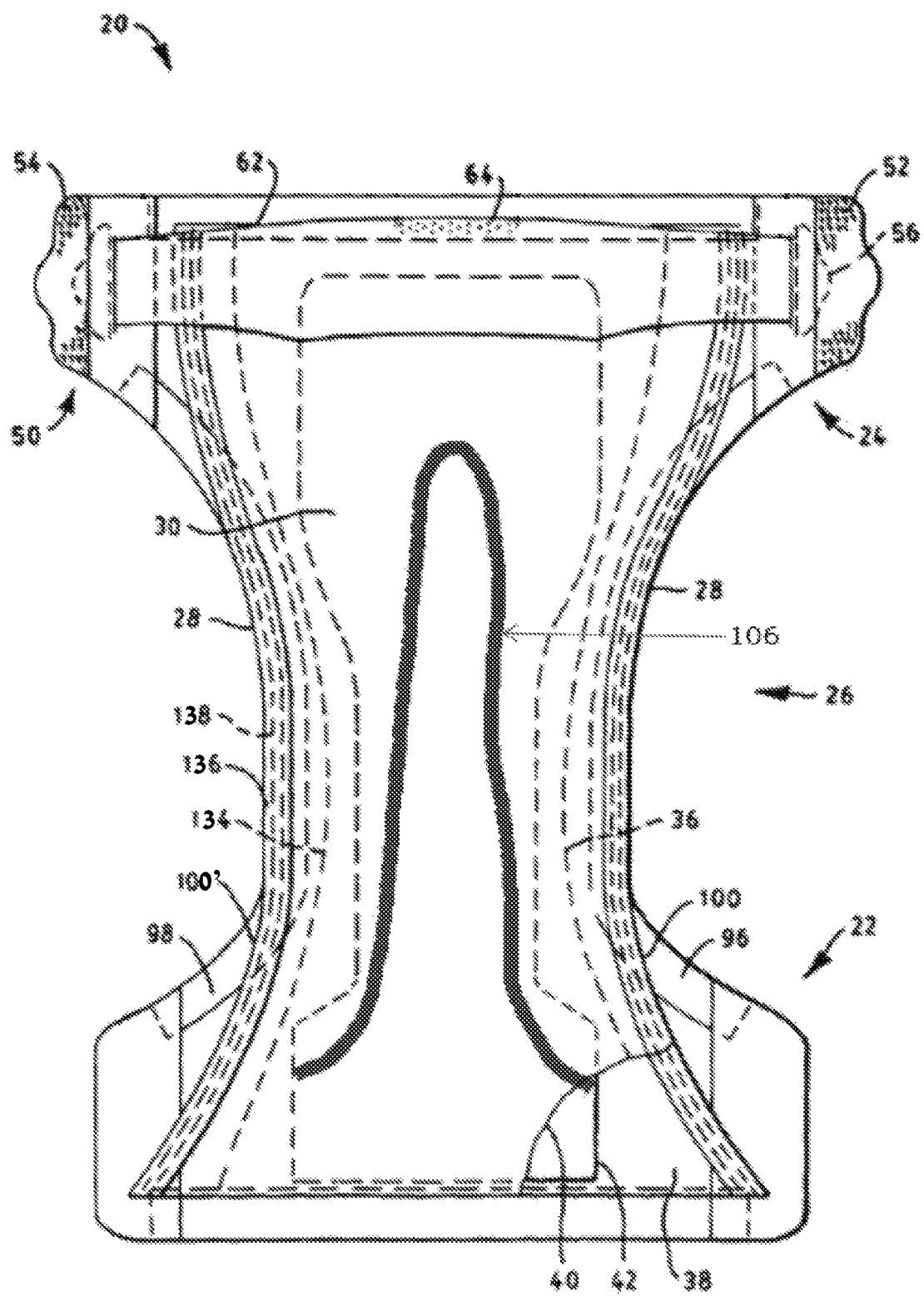
FIG. 7 shows a plan view of an absorbent article according to an embodiment herein.
Figure 8:
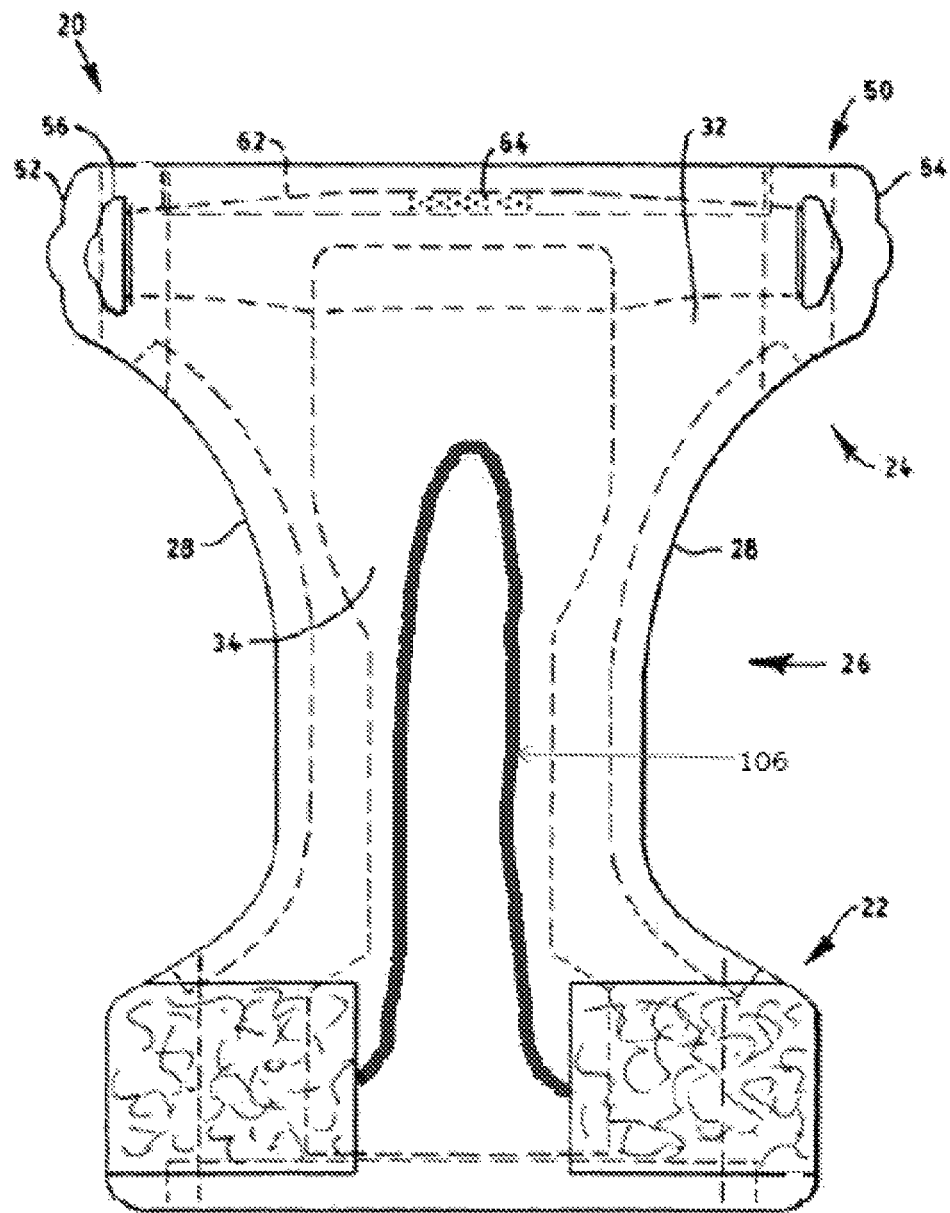
FIG. 8 shows a plan view of an absorbent article according to an embodiment herein.

As representatively illustrated in FIGS. 5-7, the diaper 20 defines a front waist region 22, a back waist region 24, a crotch region 26 which extends between and connects the front and back waist regions 22 and 24, a pair of laterally opposed side edges 28, an interior surface 30 and an outer surface 32. The front waist region 22 comprises the portion of the diaper 20 which, when worn, is positioned on the front of the wearer while the back waist region 24 comprises the portion of the diaper 20 which, when worn, is positioned on the back of the wearer. The crotch region 26 of the diaper 20 comprises the portion of the diaper 20 which, when worn, is positioned between the legs of the wearer and covers the lower torso of the wearer.

The diaper 20 includes an outer cover 34, an absorbent chassis 36 and a fastening system 50. The absorbent chassis 36 is configured to contain and/or absorb any body exudates discharged from the wearer. Whereas, the outer cover 34 and fastening system 50 are configured to maintain the diaper 20 about the waist of the wearer, conceal the absorbent chassis 36 from view, and provide a garment-like appearance. The diaper 20 may further include leg elastics 96 and 98 and containment flaps 100 and 101'. It should be recognized that individual components of the diaper 20 may be optional depending upon the intended use of the diaper 20.

As representatively illustrated in FIGS. 5-8, the laterally opposed side edges 28 of the diaper 20 are generally defined by the side edges of the outer cover 34 which further define leg openings which may be curvilinear. The waist edges of the outer cover 34 also define a waist opening which is configured to encircle the waist of the wearer when worn.

As representatively illustrated in FIGS. 5-8, the absorbent chassis 36 of the diaper 20 is suitably connected to the outer cover 34 to provide the disposable diaper 20. The absorbent chassis 36 may be connected to the outer cover 34 in manners well known to those skilled in the art. For example, the absorbent chassis 36 may be bonded to the outer cover 34 using adhesive, thermal or ultrasonic bonding techniques known to those skilled in the art. Alternatively, the absorbent chassis 36 may be connected to the outer cover 34 using conventional fasteners such as buttons, hook and loop type fasteners, adhesive tape fasteners, and the like. The other components of the diaper 20 may be suitably connected together using similar means.

Desirably, the absorbent chassis 36 is connected to the outer cover 34 only at or adjacent the waist edges of the outer cover 34 thereby creating a front attached portion, a back attached portion and an unattached portion which extends between and connects the attached portions. The unattached portion of the absorbent chassis 36 remains substantially unattached to the outer cover 34 and is generally configured to fit between the legs of the wearer and at least partially cover the lower torso of the wearer when in use. As a result, the unattached portion is generally the portion of the absorbent chassis 36 which is configured to initially receive the body exudates from the wearer when in use.

In this manner, the absorbent chassis 36 is connected to the outer cover 34 in such a manner to secure the chassis 36 in place while not adversely restricting the movement of the outer cover 34 in use. Alternatively, the absorbent chassis 36 may be attached to the outer cover 34 along the entire longitudinal length of the absorbent chassis 36 or any portion thereof or along only the outer periphery of the absorbent chassis 36.

As representatively illustrated in FIGS. 5-8, the absorbent chassis 36 according to the present disclosure may include a back sheet 38, a top sheet 40 which is connected to the backsheet 38 in a superposed relation, and an absorbent core 42 which is located between the top sheet 40 and the back sheet 38.

The absorbent chassis 36 is generally conformable and capable of absorbing and retaining body exudates. The absorbent chassis 36 may have any of a number of shapes and sizes. For example, as representatively illustrated in FIGS. 5-8, the absorbent chassis 36 may be rectangular, I-shaped or T-shaped. The size and absorbent capacity of the absorbent chassis 36 should be compatible with the size of the intended wearer and the fluid loading imparted by the intended use of the diaper 20.

The top sheet 40 of the absorbent chassis 36, as representatively illustrated in FIGS. 5-8, suitably presents a bodyfacing surface which is intended to be worn adjacent the body of the wearer and is compliant, soft feeling and nonirritating to the wearer's skin.

Further, the top sheet 40 may be less hydrophilic than the absorbent core 42, to present a relatively dry surface to the wearer, and may be sufficiently porous to be liquid permeable, permitting liquid to readily penetrate through its thickness. A suitable top sheet 40 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The top sheet 40 is suitably employed to help isolate the wearer's skin from fluids held in the absorbent core 42 of the absorbent chassis 36.

The top sheet 40 and back sheet 38 are generally adhered to one another so as to form a pocket in which the absorbent core 42 is located to provide the absorbent chassis 36. The top sheet 40 and back sheet 38 may be adhered directly to each other around the outer periphery of the absorbent chassis 36 by any means known to those skilled in the art such as adhesive bonds, sonic bonds or thermal bonds. For example, a uniform continuous layer of adhesive, a patterned layer of adhesive, a sprayed or meltblown pattern of adhesive or an array of lines, swirls or spots of adhesive may be used to affix the top sheet 40 to the back sheet 38. It should be noted that both the top sheet 40 and the back sheet 38 need not extend completely to the outer periphery of the absorbent chassis 36. For example, the back sheet 38 may extend to the outer periphery of the absorbent chassis 36 while the top sheet 40 may be attached to the back sheet 38 inboard of the outer periphery of the absorbent chassis 36, or more towards the longitudinal centerline of the diaper 20.

The absorbent core 42, as representatively illustrated in FIGS. 5-8, is positioned between the top sheet 40 and the back sheet 38 to form the absorbent chassis 36. The absorbent core 42 is desirably conformable and capable of absorbing and retaining body exudates. The absorbent core 42 may have any of a number of shapes and generally discrete layer within the matrix of hydrophilic fibers. Alternatively, the absorbent core 42 may comprise a laminate of fibrous webs and high-absorbency material or other suitable means of maintaining a high-absorbency material in a localized area.

As representatively illustrated in FIGS. 5-8, the absorbent chassis 36 of the disposable diaper 20 may include a pair of containment flaps 100 and 101' which are configured to provide a barrier to the lateral flow of body exudates. The containment flaps 100 and 101' may be located along the laterally opposed side edges of the absorbent chassis 36. Each containment flap defines an attached edge 134 and an unattached edge 136. Each of the containment flaps 100 and 101' may also include at least one elongated elastic member 138 which is adhered to the unattached edge 136 of the containment flap 100 and 101' and configured to gather the unattached edge 136 and form a seal against the body of the wearer when in use. The containment flaps 100 and 101' may extend longitudinally along the entire length of the absorbent chassis 36 or may only extend partially along the length of the absorbent chassis 36. When the containment flaps 100 and 101' are shorter in length than the absorbent chassis 36, the containment flaps 100 and 101' can be selectively positioned anywhere along the side edges 38 of the absorbent chassis 36. In a particular aspect of the disclosure, the containment flaps 100 and 101' extend along the entire length of the absorbent chassis 36 to better contain the body exudates.

Each containment flap 100 and 101' is attached to the side edges 38 of the absorbent chassis 36 such that the containment flaps 100 and 101' 2 provide a barrier to the lateral flow of body exudates. The attached edge 134 of each of the containment flaps 100 and 101' is attached to the side edges 38 of the absorbent chassis 36 while the unattached edge 136 remains unattached from the absorbent chassis 36 in at least the crotch region 26 of the diaper 20. The attached edge 134 of the containment flaps 100 and 101' may be attached to the absorbent chassis 36 in any of several ways which are well known to those skilled in the art. For example, the attached edge 134 of the flaps 100 and 101' may be ultrasonically bonded, thermally bonded or adhesively bonded to the absorbent chassis 36. In a particular aspect, the unattached edge 136 of each of the containment flaps 100 and 101' remains unattached from the side edges 38 of the absorbent chassis 36 along substantially the entire length of the unattached edge 136 to provide improved performance.

Alternatively, as representatively illustrated in FIGS. 4-7, the containment flaps 100 and 101' may be integral with the back sheet 38 or top sheet 40 of the absorbent chassis 36.

Each containment flap 100 and 101' is also configured such that the unattached edge 136 of the containment flaps 100 and 101' tends to position itself in a spaced relation away from the absorbent chassis 36 toward a generally upright and perpendicular configuration, especially in the crotch region 26 when in use. As representatively illustrated in FIGS. 5-8, the unattached edge 136 of each containment flap 100 and 101' is desirably spaced away from the absorbent chassis 36 when in use thereby providing a barrier to the lateral flow of body exudates. Desirably, the unattached edge 136 of each containment flap 100 and 101' maintains a contacting relationship with the body of the wearer while the absorbent chassis 36 may be spaced away from the body of the wearer when in use. Typically, an elastic member 138 is attached to the unattached edge 136 of each containment flap 100 and 101' to maintain the spaced away relationship between the unattached edge 136 and the absorbent chassis 36. For example, the elastic member 138 may be attached to the unattached edge 136 in an elastically contractible condition such that the contraction of the elastic member 138 gathers or contracts and shortens the unattached edge 136 of the containment flap 100 and 101'.

The disposable diaper 20 of the different aspects of the present disclosure may further include elastics at the waist edges and side edges 28 of the diaper 20 to further prevent the leakage of body exudates and support the absorbent chassis 36. For example, as representatively illustrated in FIGS. 5-8, the diaper 20 of the present disclosure may include a pair of leg elastic members 96 and 98 which are connected to the laterally opposed side edges 28 in the crotch region 26 of the diaper 20. The leg elastics 96 and 98 are generally adapted to fit about the legs of a wearer in use to maintain a positive, contacting relationship with the wearer to effectively reduce or eliminate the leakage of body exudates from the diaper 20.

The absorbent article illustrated in FIG. 9 to FIG. 12 generally represents a training pant. The absorbent article 10. The longitudinal direction 48 generally extends from the front of the absorbent article to the back of the absorbent article. Opposite to the longitudinal direction 48 is a lateral direction 49. The absorbent article 10 includes a chassis 12 that is comprised of a front portion 22, a back portion 24, and a crotch portion 26. Positioned within the crotch portion 26 and extending from the front portion 22 to the back portion 24 is an absorbent core 28.

The absorbent article 10 defines an interior surface that is configured to be placed adjacent to the body when being worn. The absorbent article 10 also includes an exterior surface opposite the interior surface. The front and back portions 22 and 24 are those portions of the article which, when worn, partially cover or encircle the waist or midlower torso of the wearer. The crotch portion 26, on the other hand, is generally positioned between the legs of the wearer when the absorbent article has been donned.

Figure 9:
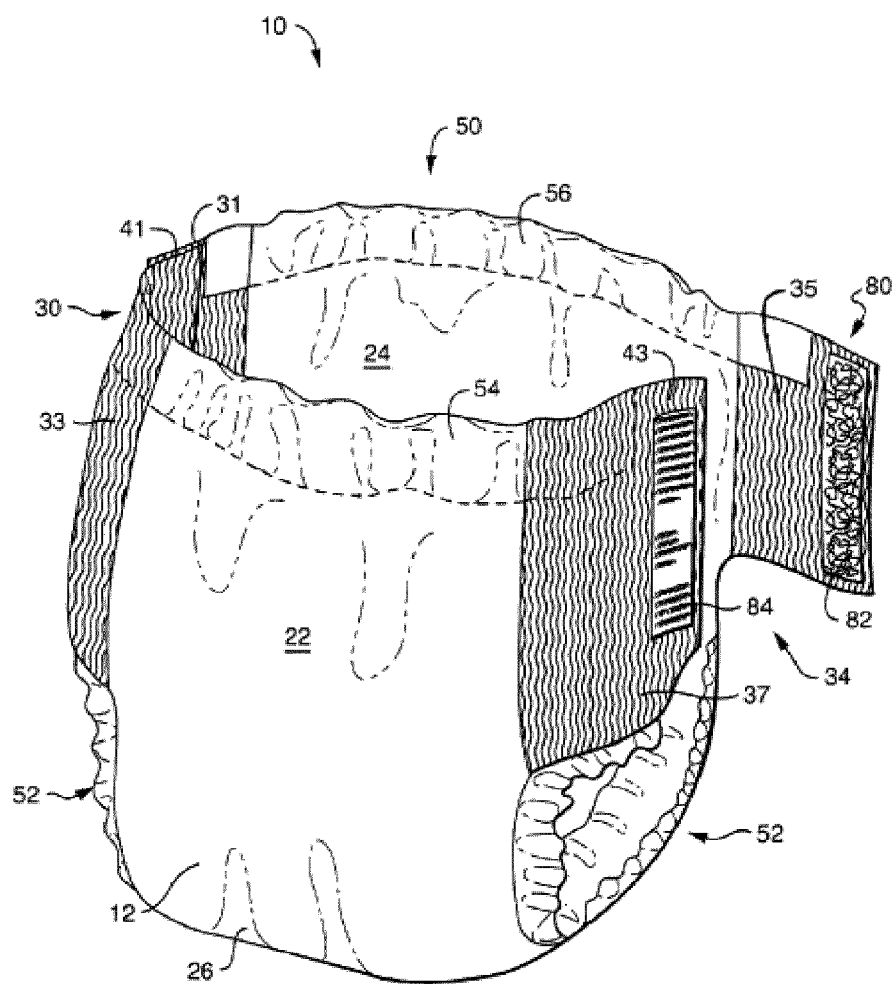
FIG. 9 shows a perspective overview of an absorbent article according to an embodiment herein.

As shown in FIG. 9, the absorbent article further includes a first side area 30 and a second side area 34. The side areas 30 and 34 connect the front portion 22 with the back portion 24. The side areas 30 and 34 can also help define the leg openings and the waist opening.

The side areas 30 and 34, in one embodiment, can be made from a stretchable or extensible material. In one embodiment, for instance, the side areas 30 and 34 are made from an elastic material. The side areas serve to form a snug but comfortable fit around the torso of a wearer. The side areas 30 and 34 can also allow for accommodating different torso circumferences.

As shown, each of the side areas 30 and 34 can be made from multiple stretchable panels. For instance, in the embodiment shown in FIG. 9, the side areas 30 and 34 are each made from two panels. As shown, for instance, the side area 30 includes a first panel 31 and a second panel 33. Similarly, the second side area 34 includes a first panel attached to a second panel 37. The panels 31 and 33 of the first side area 30 are attached together to form a first vertical attachment area 41 while the panels 35 and 37 of the second side area 34 are attached together along a second vertical attachment area 43. The attachment between the panels can be permanent or can be unfastenable and refastenable. When the panels are releasably attached together, for instance, any suitable mechanical fastener may be used. For example, in one embodiment, the panels may be releasably attached together using any suitable adhesive fastener, cohesive fastener, mechanical fastener, or the like. Suitable mechanical fastening elements can be provided by interlocking geometric shaped materials, such as hooks, loops, bulbs, mushrooms, arrowheads, balls on stems, male and female mating components, buckles, snaps, and the like.

In the embodiment illustrated in FIGS. 9-12, the panels 31 and 33 that comprise the first side area 30 and the panels 35 and 37 that comprise the second side area 34 are joined together using a fastening system 80 that includes laterally opposite first fastening components 82 adapted for refastenable engagement to corresponding second fastening components 84. For instance, in one embodiment, a front or outer surface of each of the fastening components 82, 84 includes a plurality of engaging elements. The engaging elements of the first fastening components 82 are adapted to repeatably engage and disengage corresponding engaging elements of the second fastening components 84 to releasably secure the absorbent article in its 3-dimensional configuration.

In an embodiment for instance, the first fastening components 82 include loop fasteners and the second fastening components 84 include complementary hook fasteners. Alternatively, the first fastening components 82 may include hook fasteners and the second fastening components 84 may be complementary loop fasteners. In another aspect, the fastening components 82 and 84 can be interlocking similar surface fasteners, or adhesive or co-adhesive fastening elements such as an adhesive fastener and an adhesive-receptive landing zone or material.

As described above, in an alternative embodiment, the panels that comprise the side areas may be permanently attached together. For instance, referring to FIG. 10, an alternative embodiment of an absorbent article 10 is shown. Like reference numerals have been used to indicate the same or similar elements. As shown, the absorbent article 10 in FIG. 10 includes a first side area 30 comprised of panels 31 and 33 and a second side area 34 comprised of panels 35 and 37. The first side panel 30 defines a first vertical attachment area 41 where the panels 31 and 33 are permanently bonded together. Similarly, the second side area 34 defines a second vertical attachment area 43 where the panels 35 and 37 have been permanently attached together. In this embodiment, the vertical attachment areas comprise seams. The seams, for instance, can be constructed in any suitable manner. For instance, the vertical seam may comprise a lap seam, a butt seam, or any other suitable configuration. The seams can be formed by attaching the panels together using any suitable method or technique. For example, the panels can be permanently attached together using ultrasonic bonding, thermal bonding, adhesive bonding, and/or pressure bonding. In still another alternative embodiment, the separate panels can be sewn together.

Figure 10:
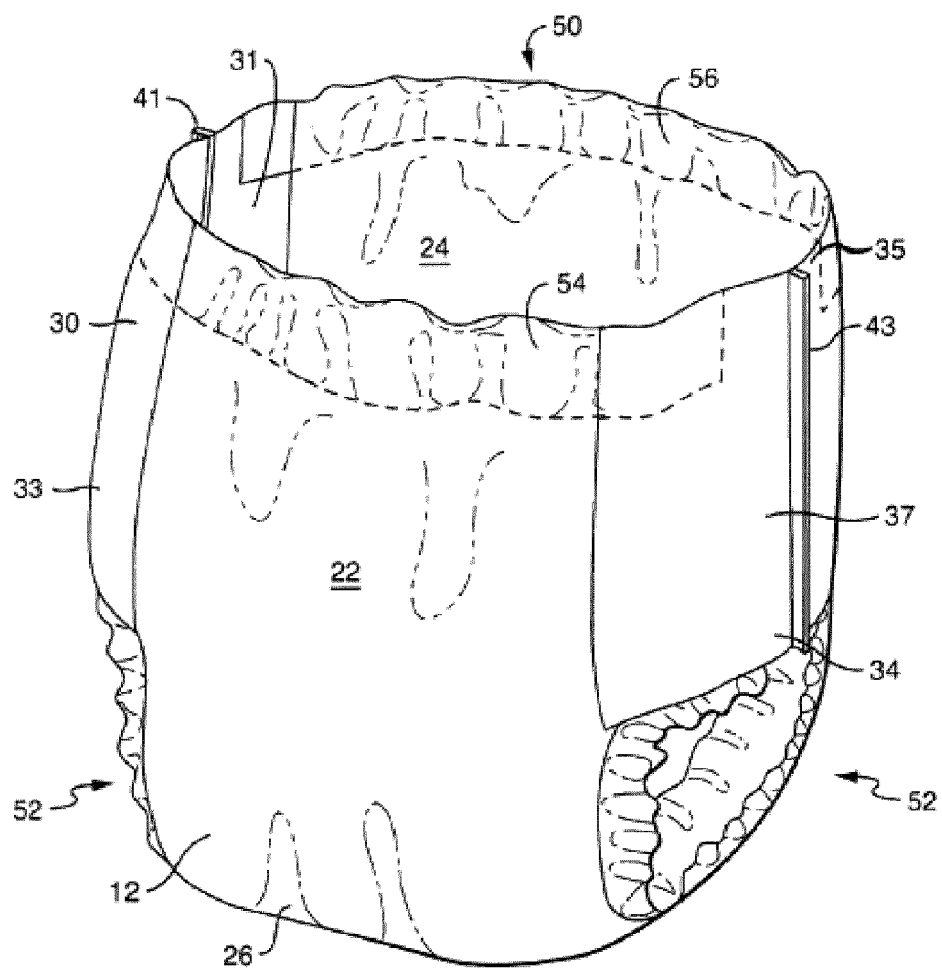
FIG. 10 shows a perspective overview of a product according to an embodiment herein.

As shown in FIGS. 9 and 10 when the side areas 30 and 34 are in a fastened position, the front and back portions 22 and 24 are connected together to define a 3-dimensional pants configuration having a waist opening 50 and a pair of leg openings 52. The side areas 30 and 34, upon wearing of the absorbent article 10, thus include the portions of the article which are positioned on the hips of the wearer and, in one embodiment, define the upper edge of the leg openings 52.

As described above, the chassis 12 can, in one embodiment, include an outer cover 40 and a top sheet 42 as shown particularly in FIGS. 11 and 12. Depending upon the embodiment, the outer cover 40 and the top sheet 42 can comprise a unitary single-piece of material or can comprise multiple pieces of material bonded together. The top sheet 42 may be joined to the outer cover 40 in a superimposed relation using, for instance, adhesives, ultrasonic bonds, thermal bonds, pressure bonds or other conventional techniques. The top sheet 42 may suitably be joined to the outer cover 40 along the perimeter of the chassis 12 to form a front waist seam 62 and a back waist seam 64. The top sheet 42 may also be joined to the outer cover 40 to form a pair of side seams 61. The top sheet 42 can be generally adapted, i.e., positioned relative to the other components of the absorbent article 10, to be disposed toward the wearer's skin when donned. As described above, the chassis 12 also includes the absorbent core 28 which is disposed between the outer cover 40 and the top sheet 42 for absorbing liquid body exudates exuded by the wearer.

In accordance with the present disclosure, the absorbent article 10 further includes one or more extended waistbands that are intended to improve product appearance, to improve fit, and/or make the product feel more like real underwear. As shown in the figures, for instance, the absorbent article 10 can include a back waistband 56, a front waistband 54, or can include both a front waistband and a back waistband. As shown, for instance, the back waistband 56 extends over the entire back portion 24 of the chassis 12 and terminates at each end on the side areas 30 and 34.

It is supposed that the present disclosure is not restricted to any form of realization described previously and that some modifications can be added to the presented example of fabrication without reappraisal of the appended claims. For example, although the above example makes reference to the embodiments of FIG. 5 to FIG. 8, similar structures may be found in other embodiments as illustrated in FIG. 9 to FIG. 12, and further feminine care articles such as those of FIG. 13 and FIG. 14. Moreover, although the example and figures relate to baby diapers and pants, the same remains applicable to incontinence diapers and pants for adults albeit with some structural alterations which would be apparent to a person skilled in the art.

Example 2

Figure 13:
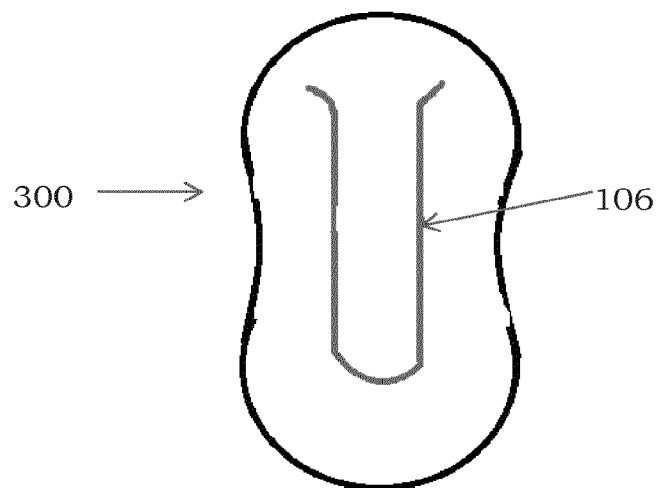
FIG. 13 shows a diagrammatic view of an absorbent article according to an embodiment herein.
Figure 14:
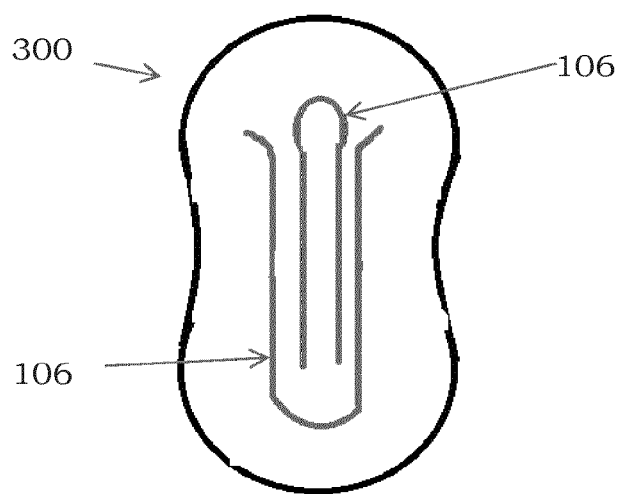
FIG. 14 shows a diagrammatic view of an absorbent article according to an embodiment herein.

Referring to FIG. 13 and FIG. 14, the absorbent articles may be of the sanitary napkin or panty liner type.

The structure of the napkin or panty liner may vary in construction as long as a core as described herein is used. Generally such napkin or panty liner include a laminate comprising a backsheet, an absorbent core (with or without three-dimensional absorbent material) and optionally a liquid distribution layer (ADL) positioned between the topsheet and the absorbent core.

As shown in FIG. 14 the interconnected channel 106 may be in a plurality and be substantially concentric with respect to each other and may be inverse in shape about an axis parallel to the width of the core. Although such pattern is illustrated as an example for use in a core for a sanitary napkin or a panty liner 300, such shape may be equally applied and is encompassed in the teaching of cores for diapers and pants (whether for babies or incontinence for adults) herein.

The invention claimed is:

1. An absorbent core (101) comprising:
   a front portion (122);
   a back portion (124);
   a crotch portion (126) positioned between the front portion (122) and the back portion (124); and
   a longitudinal axis extending along a length of said core (101) and crossing said front, crotch and back portions (122, 126, 124), the absorbent core (101) having a width extending perpendicular to said length and a perimeter comprising at least two opposing ends (102, 103) and at least two opposing sides (104, 105) positioned between said ends (102, 103) characterized in that the absorbent core (101) comprises one or more substantially interconnected channels (106) extending through the crotch portion (126) along and substantially parallel to the longitudinal axis and further extending along at least a portion of said width of the core from one side of the core to the other, wherein said one or more substantially interconnected channels (106) are substantially free of three-dimensional absorbent material and comprises a first nonwoven web bonded to a second nonwoven web by one or more adhesives, and wherein each substantially interconnected channel (106) comprises:
   a first channel portion (107) extending substantially along the longitudinal axis proximal to a first side (104) of the core (101);
   a second channel portion (108) extending substantially along the longitudinal axis proximal to a second side (105) of the core (101); and
   at least one connecting channel portion (109) in fluid communication with said first and second channel portions (107, 108), and wherein the connecting channel portion (109) extends substantially along the width of said core (101) forming a closed end shape within a surface of said core (101) along a plane parallel to the longitudinal axis, said closed end being substantially curvilinear in shape forming a convex shape between the first and second channel portions (107, 108).

2. The absorbent core (101) according to claim 1 wherein the closed end is positioned opposite to an open end shape formed by non-connected first and second terminal positions (110, 111) of the first and second channel portions (107, 108) respectively, of the substantially interconnected channel (106), wherein said non-connected first and second terminal positions (110, 111) are distal to each other and proximal to the first and second sides (104, 105) of said core (101) respectively.

3. The absorbent core (101) according to claim 2 wherein said terminal positions (110, 111) face away from each other to form a funnel-shaped gap therebetween.

4. The absorbent core (101) according to claim 1 having a first distance ($d_1$) between the first channel portion (107) and the second channel portion (108), a second distance ($d_2$) between the first channel portion (107) and the second channel portion (108), wherein the first distance ($d_1$) is proximal to the front portion (122) of the core (101) and the second distance ($d_2$) is proximal to the back portion (124) of the core (101), and wherein the first distance ($d_1$) is greater than the second distance ($d_2$).

5. The absorbent core (101) according to claim 4, wherein the first distance ($d_1$) is at least $1.5d_2$.

6. The absorbent core (101) according to claim 4, wherein the first distance ($d_1$) is from $1.8d_2$ to $3d_2$.

7. The absorbent core (101) according to claim 1 comprising the first nonwoven web; the second nonwoven web; and a three-dimensional absorbent material positioned between the first and second nonwoven webs to form an absorbent core laminate.

8. The absorbent core (101) according to claim 7, wherein the first nonwoven web is in the form of a backsheet and the second nonwoven web is in the form of a topsheet.

9. The absorbent core (101) according to claim 7, wherein the three dimensional absorbent material comprises a fibrous web.

10. The absorbent core (101) according to claim 7, wherein the three dimensional absorbent material comprises a predetermined amount of super absorbent polymer dispersed therethrough.

11. The absorbent core (101) according to claim 1 comprising a plurality of substantially interconnected channels.

12. The absorbent core (101) according to claim 11 wherein the plurality of substantially interconnected channels are arranged in a substantially concentric manner.

13. The absorbent core (101) according to claim 1 further comprising one or more disconnected channels.

14. The absorbent core (101) according to claim 13 wherein at least a portion of the one or more disconnected channels are arranged concentrically to the one or more substantially interconnected channels.

15. The absorbent core (101) according to claim 1 wherein the substantially interconnected channels (106) have a regular depth, said depth being measured on an axis perpendicular to both the longitudinal axis and the axis along the width of the core (101).

16. The absorbent core (101) according to claim 1 wherein the cross-section of said channels (106) is selected from the group consisting of curved, polygonal and combinations thereof.

17. The absorbent core (101) according to claim 1 wherein the substantially interconnected channels (106) have an irregular depth, said depth being measured on an axis perpendicular to both the longitudinal axis and the axis along the width of the core (101).

18. The absorbent core (101) according to claim 1, wherein said one or more substantially interconnected channels (126) are symmetric about the longitudinal axis.

19. The absorbent core (101) according to claim 1, wherein said one or more substantially interconnected channels (126) are asymmetric about the longitudinal axis.

20. An absorbent article (10, 20, 300) comprising a core (101) according to claim 15, said article being selected from disposable diapers or diaper pants; disposable incontinence diapers or diaper pants; sanitary napkins; and panty liners.

21. The absorbent article (10, 20, 300) according to claim 20, wherein the channels remain visible both before and after use of the article.

22. The absorbent article (10, 20, 300) according to claim 20, wherein the channels are more visible after use than before use of the article.

\* \* \* \* \*